US010319056B1

(12) United States Patent
Perez et al.

(10) Patent No.: US 10,319,056 B1
(45) Date of Patent: Jun. 11, 2019

(54) BIASED TASK ASSIGNMENTS BASED ON GEOTRACKING OF DISCHARGE VEHICLES

(71) Applicant: HCA Holdings, Inc., Nashville, TN (US)

(72) Inventors: Gabriel O. Perez, Miramar, FL (US); Michael A. Houston, Parkland, FL (US)

(73) Assignee: HCA Holdings, Inc., Nashville, TN (US)

( * ) Notice: Subject to any disclaimer, the term of this patent is extended or adjusted under 35 U.S.C. 154(b) by 747 days.

(21) Appl. No.: 14/957,911

(22) Filed: Dec. 3, 2015

Related U.S. Application Data

(60) Provisional application No. 62/087,663, filed on Dec. 4, 2014.

(51) Int. Cl.
  *G06Q 50/30* (2012.01)
  *G06F 19/00* (2018.01)
  *G16H 40/20* (2018.01)

(52) U.S. Cl.
  CPC ......... *G06Q 50/30* (2013.01); *G06F 19/3418* (2013.01); *G16H 40/20* (2018.01)

(58) Field of Classification Search
  CPC .......................................... G06Q 10/00–50/00
  USPC ................................................. 705/7.11–7.42
  See application file for complete search history.

(56) References Cited

U.S. PATENT DOCUMENTS

| | | | | |
|---|---|---|---|---|
| 6,117,073 A | * | 9/2000 | Jones | G06Q 50/22 600/300 |
| 7,734,479 B2 | * | 6/2010 | Rosow | G06Q 10/02 705/2 |
| 7,743,303 B2 | * | 6/2010 | Nobunaga | G11C 29/76 714/6.13 |
| 9,754,335 B2 | * | 9/2017 | Jourdan | G06Q 50/22 |
| 2008/0154691 A1 | * | 6/2008 | Wellman | G05D 1/0282 705/7.26 |
| 2008/0154712 A1 | * | 6/2008 | Wellman | G05D 1/0282 235/384 |
| 2008/0164998 A1 | * | 7/2008 | Scherpbier | G06Q 10/06 340/539.13 |

* cited by examiner

*Primary Examiner* — Alan S Miller
(74) *Attorney, Agent, or Firm* — Kilpatrick Townsend & Stockton, LLP

(57) ABSTRACT

Systems, non-transitory computer-readable media, and computer-implemented methods are provided for using location data of discharge vehicles for management of distributions of task assignments. Systems, non-transitory computer-readable media, and computer-implemented methods are provided for collecting task specifications and identifying appropriate task-performing resources. Systems, non-transitory computer-readable media, and computer-implemented methods are provided for using location data of discharge vehicles for electronically adjusting scheduled tasks. Systems, non-transitory computer-readable media, and computer-implemented methods are provided for assigning tasks based on empirical performance assessments of resource-allocation systems.

20 Claims, 12 Drawing Sheets

BIASED TASK ASSIGNMENTS BASED ON GEOTRACKING OF DISCHARGE VEHICLES

RELATED APPLICATIONS

This application claims benefit under 35 U.S.C. § 119(e) to U.S. Provisional Patent Application No. 62/087,663, filed Dec. 4, 2014, the disclosure of which is incorporated by reference herein in its entirety for all purposes.

BACKGROUND

Certain embodiments of the present disclosure relate generally to geotracking and in particular to systems and methods for biased task assignments based on geotracking of discharge vehicles.

According to conventional practices, when special needs transportation must be coordinated, staff members of an originating special needs facility, of a destination special needs facility, and of transportation companies typically coordinate the transportation via a series of telephone calls. For example, the special needs transportation may correspond to transporting a patient by ambulance between hospitals and/or other medical facilities. In some cases, a transfer center may also be involved to act as a middleman between several transportation companies and the special needs facilities.

To request a transfer, a first staff member of a first special needs facility relays a request for transportation to one or more other parties by telephone. The first staff member must communicate all the details of the need, such as details of a person to be transported, a pickup location, a pickup time, a destination, special circumstances, account details, policy details, etc. One or more other staff members (of a transfer center, a transportation company, or a destination facility) typically type the received information, entering the information into a system that is separate from any system of the first special needs facility. In some cases, where medical facility personnel call transportations companies directly, sometimes several ambulance companies must be contacted to coordinate a transfer and/or to reap the benefits of competition. In the case of transfer center involvement, transfer center staff then telephones a transportation company and further relays the information about the transfer. Thus, multiple telephone calls and multiple conversations, at a minimum, are required for the for the setup of the transfer.

After setup of the transfer, coordination often ends. The medical facilities are ignorant of any statuses of the transport vehicle, of ETAs (estimated times of arrival), of whether the transport vehicle is on-time, early or late, of whether there are any plan changes, etc., unless a staff member picks up the telephone again and calls the transfer center, the transport vehicle, or the transportation company. Even then, one more additional phone calls or radio communications may be necessary to gather a modicum of current information.

Thus, the communications throughout the process are in large part by word-of-mouth. Moreover, in order to determine options and coordinate logistics that take into account different needs, different availabilities, different capabilities, and difference performances, an expert is necessary to make judgment calls and attempt to somewhat shepherd the transfer. As a consequence of all these factors, the conventional practices are error-prone, knowledge-deficient, time-consuming, and inefficient.

Accordingly, there is a need for systems and methods for biased task assignments based on geotracking of discharge vehicles. This and other needs are addressed by the present disclosure.

BRIEF SUMMARY

Certain embodiments of the present disclosure relate generally to geotracking and in particular to systems and methods for biased task assignments based on geotracking of discharge vehicles.

In one aspect, a system, non-transitory computer-readable media, and a computer-implemented method are provided for using location data of discharge vehicles for management of distributions of task assignments. The provided features may include any one or combination of the following. A first time corresponding to performance of a defined portion of a task assigned to a discharge vehicle may be identified. The first time may be compared to a target arrival time. A corresponding resource-allocation system associated with the discharge vehicle may be identified. A metric for task performance for the corresponding resource-allocation system may be adjusted based on the comparison of the first time to the target arrival time. A task to be assigned to a resource-allocation system of a set of resource-allocation systems may be detected. The set of resource-allocation systems may include the corresponding resource-allocation system. An assignment of the task may be biased based on the metric for the corresponding resource-allocation system.

In another aspect, a system, non-transitory computer-readable media, and a computer-implemented method are provided for collecting task specifications and identifying appropriate task-performing resources. The provided features may include any one or combination of the following. An identifier of a load corresponding to a task may be detected. A characteristic of the load may be retrieved from an electronic record. A type of task-performing resource configured to accept loads having the characteristic may be identified. A target time for performing the task may be identified. A first signal that identifies the type of task-performing resource and the target time may be generated. One or more resource-allocation systems configured to coordinate task performances may be identified. The first signal may be transmitted to each of the one or more resource-allocation systems. A second signal may be received from a resource-allocation system of the one or more resource-allocation systems that is indicative of an offer to accept an assignment of the task.

In yet another aspect, a system, non-transitory computer-readable media, and a computer-implemented method are provided for using location data of discharge vehicles for electronically adjusting scheduled tasks. The provided features may include any one or combination of the following. Location-based data that is based on a location of a discharge vehicle may be received from a resource-allocation system. A timeliness of performance of a first task based on the location-based data may be predicted. A target efficiency metric reflecting a target efficiency of local task performance may be accessed. A second task identified in a flexible task schedule may be identified. A performance time for the second task to be performed may be determined based on the predicted timeliness of performance of the first task and the target efficiency metric. A signal with an instruction to perform the second task at the determined performance time may be transmitted.

In still another aspect, a system, non-transitory computer-readable media, and a computer-implemented method are provided for assigning tasks based on empirical performance assessments of resource-allocation systems. The provided features may include any one or combination of the following. A task requiring assignment to a resource-allocation system such that the resource-allocation system is to configure a resource associated with the resource-allocation system to perform the task may be identified. A target time for at least part of the task to be completed may be identified. A first signal corresponding to the task that identifies the target time and is indicative that the task is requiring assignment may be generated. The first signal may be transmitted to each resource-allocation system of the set of resource-allocation systems. A second signal may be received from each of a plurality of resource-allocation systems in the set of resource-allocation systems that corresponds to an offer to accept an assignment of the task. A performance metric for each resource-allocation system in the plurality of resource-allocation systems that is indicative of a reliability of performance of tasks previously assigned to the resource-allocation system may be accessed. A resource-allocation system may be selected, based on the accessed performance metrics, from amongst the plurality of resource-allocation systems to be assigned the task. A third signal that indicates that the task is being assigned to the selected resource-allocation system may be generated. The third signal may be transmitted to the selected resource-allocation system.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

DETAILED DESCRIPTION

The ensuing description provides preferred exemplary embodiment(s) only and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes can be made in the function and arrangement of elements without departing from the spirit and scope as set forth in the appended claims.

Figure 1:
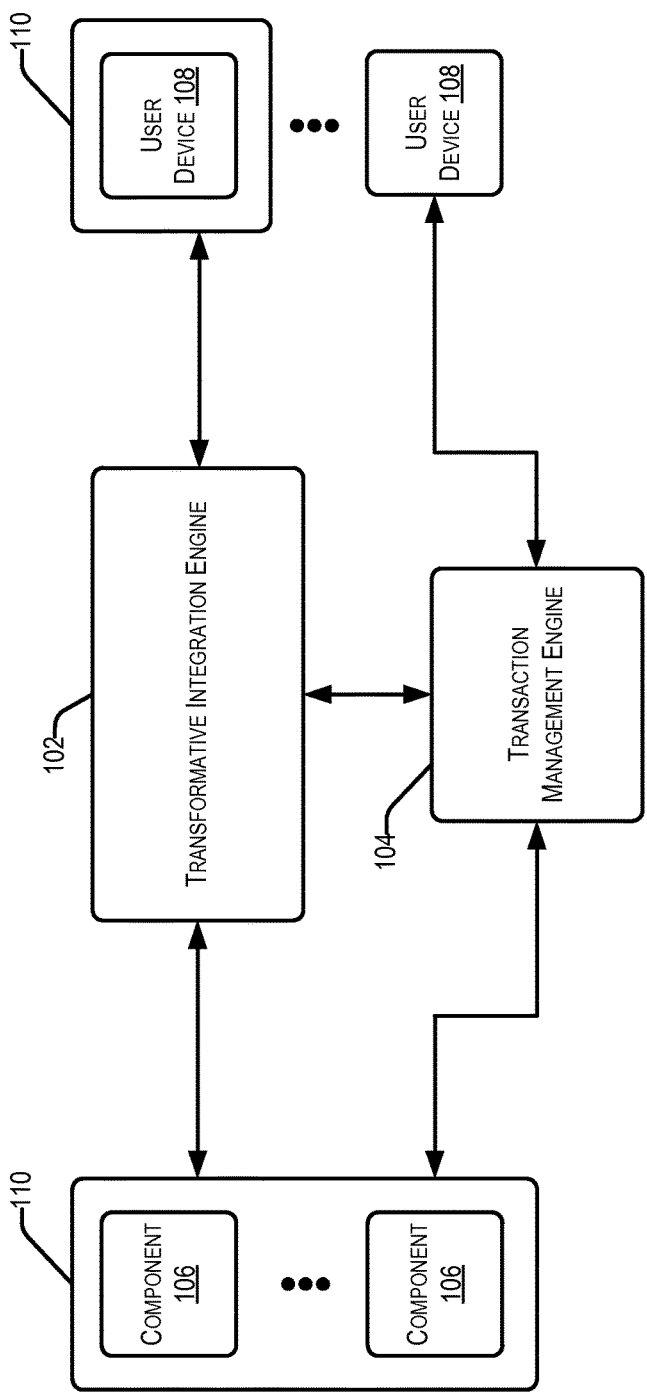
FIG. 1 illustrates a block diagram of an embodiment of a medical provider network, in accordance with certain embodiments of the present disclosure.

Referring first to FIG. 1, a block diagram of an embodiment of a medical provider network 100 is illustrated. The medical provider network 100 includes a plurality of elements connected with directional arrows. The directional arrows not only indicate that the elements are connected, but also indicate the direction that data may flow with respect to the various elements. For example, data may flow between the following elements of the medical provider network 100: a transformative integration engine 102 and a transaction management engine 104.

Generally, the transformative integration engine 102 is configured to collect and aggregate medical-related data from components of the medical provider network 100 and components outside of the medical provider network 100. Once the transformative integration engine 102 collects and aggregates the medical-related data, it may perform one or more operations with respect to the data and store it in a data store. This stored medical-related data can then be accessed by components within and without the medical provider network 100.

The medical-related data is transmitted throughout the medical provider network 100 in accordance with any suitable transmission protocol. Generally, the transaction management engine 104 is configured to manage the flow of such transmissions within the medical provider network 100. Thus, the transaction management engine 104 receives indications of transmissions of medical-related content and tracks the origination locations of the transmissions, the destination locations of the transmissions, and any locations there between.

The medical provider network 100 includes one or more components 106 and one or more user devices 108. The one or more components 106 are configured to share medical-related data with the transformative integration engine 102, the transaction management engine 104, and each other via one or more communication networks. The one or more user devices 108 are configured to access medical-related data collected by the transformative integration engine 102 and provide their own medical-related data. Users of the one or more user devices 108 may use such medical-related data to help the users make medical decisions. While the one or more components 106 and the one or more user devices 108 are illustrated as communicating via the transformative integration engine 102 and/or the transaction management engine 104, this specification is not so limited. For example, each of the one or more components 106 may communicate with each of the one or more user devices 108 directly via other or the same communication networks. Each of the one or more components 106 of the medical provider network 100 is an example of a device, medical equipment, a lab system, a business terminal, a clinical terminal, or the like that can receive and/or provide medical-related data as further detailed herein. Each of the one or more user devices 108 is an example of a user device that can receive and/or provide medical-related data as further detailed herein. In some examples, at least some of the one or more user devices 108 may function similar to at least some of the one or more components 106 and vice-versa. In other words, each of the one or more user devices 108 and each of the one or more components 106 may both provide data and access data within the medical provider network 100.

In some examples, the one or more components 106 are each associated with one or more medical provider organizations within the same or different medical provider networks. For example, certain ones of the one or more components 106 may be associated with a first medical provider organization, while other ones of the one or more components 106 may be associated with a second medical provider organization. Additionally, each of the one or more components 106 may be associated with a medical care facility 110. The medical care facility 110 illustrates an example of one medical care facility. The medical provider network 100, however, may include many different types of medical care facilities (e.g., urgent care facilities, outpatient facilities, hospitals, clinics, and medical record service facilities) including many different types of components. In some examples, the one or more components 106 are not associated with one of the medical care facilities 110, but instead are included as part of an information systems company that manages medical-related data such as electronic medical records.

The one or more components 106, irrespective of which medical provider organization each belongs to, may be capable of receiving, generating, processing and/or transmitting medical-related data. Examples of the one or more components 106 include, for example, a user device (e.g., computer, mobile device, smart phone, laptop, electronic badge, set-top box, thin client device, tablet, pager, and other similar user devices), clinical lab equipment (e.g., fluid processing device, chemistry analysis device, coagulation analysis device, DNA analysis device, genetic analysis device, urinalysis device, hematology analysis device, immunology analysis device, and other similar lab equipment), medical equipment (e.g., surgery tools, imaging machines, and other similar medical devices), business and/or administrative device that can receive input from (for example) a nurse, administrator, receptionist, secretary or assistant (e.g. server, computer, mobile device, smart phone, laptop, electronic badge, set-top box, thin client device and other similar business and/or administrative devices), and other similar devices capable of generating medical-related data. The one or more components 106 also includes entities that collect, aggregate, and store medical-related data. Some of these entities may be third-parties that make medical-related data available to the transformative integration engine 102.

The one or more components 106 provide medical-related data using one or more formats, some of which can be proprietary. For example, a magnetic resonance imaging (MRI) machine (e.g., one of the one or more components 106) manufactured by company A, located within a first medical care facility (e.g., the medical care facility 110), and belonging to a first medical provider organization, may save and transfer data in a first format. An MRI machine (e.g., one of the one or more components 106) manufactured by company B, located within the first medical care facility (e.g., the medical care facility 110), and belonging to the first medical care provider, may save and transfer data in a second format. In some examples, medical-related data from certain components is transformed, translated, or otherwise adjusted to be recognizable by the transformative integration engine 102. Thus, continuing with the example from above, when the MRI machines manufactured by companies A and B are located within the first medical care facility belonging to the first medical care provider, they may nevertheless save and transfer data in different formats. In some examples, the one or more components 106 communicate using the Health Level-7 (HL7) standard for hospital information systems or any other suitable format.

The transmission of medical-related data from the one or more components 106 to the transformative integration engine 102 may be triggered by a variety of different events. For example, the medical-related data may be transmitted periodically, upon detection of an event (e.g., completion of an analysis or end of a procedure), upon detection of an event defined by a rule (e.g., a user-defined rule), upon receiving user input triggering the transmission, or upon receiving a data request from the transformative integration engine 102. Each transmission can include, e.g., a single record pertaining to a single patient, procedure, or analysis or multiple records pertaining to multiple patients, procedures, or analyses.

In some examples, at least some of the one or more user devices 108 are associated with the medical care facility 110. At least some of the one or more user devices 108 may not be associated with the medical care facility 110 or any other medical care facility. Similar to the one or more components 106, the one or more user devices 108 may be capable of receiving, generating, processing and/or transmitting medical-related data. Examples of the one or more user devices 108 include, for example, a computer, a mobile device, a smart phone, a laptop, an electronic badge, a set-top box, a thin client device, a tablet, a pager, and other similar user devices). The one or more user devices 108 may differ from the one or more components 106 because the one or more user devices 108 may be configured to run one or more applications developed for interacting with the medical-related data collected by the transformative integration engine 102. For example, those user devices of the one or more user devices 108 that are not associated with the medical care facility 110 may be configured to run one or more third-party applications that may rely in part on the medical-related data gathered by the transformative integration engine 102.

Each of the one or more components 106 and the one or more user devices 108 may be utilized by one or more users (not shown). Each of the one or more users may be associated with one or more medical provider organizations. For example, one of the one or more users can be associated with a medical provider organization as a result of being employed by the organization, physically located at a location of the organization, being an agent of the organization or receiving a medical service from the organization.

The connections between the one or more components 106 and the one or more user devices 108 and the transformative integration engine 102 and the transaction management engine 104 are illustrated by a plurality of bi-directional arrows indicating that medical-related data may flow therebetween. The medical-related data flows in either direction within the medical provider network 100 (e.g., from the transformative integration engine 102 and the transaction management engine 104 towards the one or more components 106 and/or the one or more user devices 108 or to the transformative integration engine 102 and the transaction management engine 104 from the one or more components 106 and/or the one or more user devices 108). The connections between the one or more components 106 and the one or more user devices 108 and the transformative integration engine 102 and the transaction management engine 104 can include any suitable network connection. A connection can be configured to support communication over a wireless medium, e.g., using Wi-Fi (IEEE 802.11 family standards), Zigbee, Bluetooth® (a family of standards promulgated by Bluetooth SIG, Inc.), Bluetooth Low Energy or other protocols for wireless data communication. In some instances, a connection can include a wired connection.

In some examples, the one or more components 106 and the one or more user devices 108 may communicate with the transformative integration engine 102 and the transaction management engine 104 via different information formats, different proprietary protocols, different encryption techniques, different languages, different machine languages, and the like. As will be discussed with reference to FIG. 2, the transformative integration engine 102 is configured to receive these many different communications from the one or more components 106, and in some examples from the one or more user devices 108, in their native formats and transform them into any of one or more formats. The received and/or transformed communications can be transmitted to one or more other devices (e.g., the transaction management engine 104, an entity device and/or a user device) and/or locally or remotely stored. In some examples, the transformative integration engine 102 receives medical-related data in the HL7 format or conforming to any other suitable format and/or is configured to transform received data to conform with the HL7 format.

In some examples, the medical provider network 100 may not include the transformative integration engine 102, or may include part of the functionality described herein. For example, when the communications between the one or more user devices 108 and between the one or more components 106 are in the same format, the transformative integration engine 102 may not be required to transform the communications into other formats.

As used herein, medical-related data can include, for example, health information that is created or received by a health care provider, a processed or unprocessed version of medical data detected by medical equipment, and/or user-identified data. Medical-related data can include information that identifies a patient, such as personal information and/or demographic information. For example, the information can identify a patient's name, age, sex, race, physical address, phone number, email address and/or social security number. Medical-related data may include information collected by a health plan, a public health authority, an employer, a life insurer, a school or university, or a health care clearinghouse that relates to the past, present, or future physical or mental health or condition of any individual.

Medical-related data can include financial and/or insurance information corresponding to the patient. For example, the information can identify an insurance company, insurance plan, member identification number, group number, insurance contact information (e.g., address and/or phone number), deductible information, out-of-pocket information, copay information, an employer, an occupation and/or salary information.

Medical-related data can include medical-history information, such as past diagnoses, past or present symptoms or past procedures and/or corresponding dates (e.g., of diagnoses, symptom initiations and/or procedures). Medical-related data can identify past or present medications being taken by or having been prescribed to the patient and corresponding dates. In some examples, the medical-related data can identify orders pharmacology orders, whether associated with a patient, doctor, or otherwise.

Medical-related data can include an identification of one or more medical services having been, being or having been requested by a patient. A medical service can include, for example, an evaluation performed by a medical care professional, a medical test, a surgery and/or other procedure. Medical-related data can identify a medical test or analysis that was performed or prescribed and/or a result of the test or analysis. For example, information can indicate that a test (e.g., lab test, MRI, x-ray, CT scan, echocardiography, EKG, EEG, EMG, or ultrasound) was performed on a particular date and/or by a particular entity and can further include a processed and/or unprocessed result of the test (e.g., a count or level; an indication as to whether a test result is normal; and/or an indication as to whether a particular feature (e.g., a fracture, tumor, lesion, slowed nerve conduction) was observed and/or a magnitude of the feature).

Medical-related data can identify one or more care providers or institutions. The care provider and/or institution can be one associated with recent or past care and/or with the patient. For example, data can be transmitted for a patient admitted in Hospital A and being treated by Specialist B, though the data can also identify that the patient's primary care physician is Doctor C.

Medical-related data may, or may not, selectively pertain to a particular patient. For example, non-patient-specific data may include a price of a prescription, a recommended or approved dosing schedule for a medication, a work schedule for a physician, an acceptance criteria for a clinical study, Non-patient-specific data can include information pertaining to the operation of a medical care facility, financial information, administrative information, and generic clinical information.

Medical-related data can, depending on the implementation, include individually identifiable health information and/or de-identified information. Individually identifiable health information includes, for example, health information, including demographic information collected from an individual that is created or received by a health care provider, health plan, employer, or health care clearinghouse; and that relates to the past, present, or future physical or mental health or condition of an individual, the provision of health care to an individual, or the past, present, or future payment for the provision of health care to an individual; and that identifies the individual; or, with respect to which there is a reasonable basis to believe, can be used to identify the individual. De-identified information includes information that cannot be used on its own or with other information to identify a person to whom the information belongs.

As used herein, medical-related data can include protected health information, which can include individually identifiable health information that is transmitted by electronic media, maintained in electronic media, or transmitted or maintained in any other form or medium. Examples of protected health information, include, for example any information about health status, provision of health care, or payment that can be linked to a particular patient and may include any of the following information capable of identifying the patient: names, geographic identifiers, dates directly relating to the patient, phone numbers, fax numbers, email addresses, social security numbers, medical record numbers, health insurance beneficiary numbers, account numbers, certificate/license numbers, vehicle identifiers and serial numbers, device identifiers and serial numbers, web Uniform Resource Locators, Internet Protocol addresses, biometric identifiers (e.g., finger, retinal, and voice prints), full face photographic images and any comparable images, and any other unique identifying number, characteristic, or code.

The one or more components 106 of the medical care facility 110 can include and/or has access to a local or remote memory for storing generated medical-related data. In some examples, the medical-related data is stored by one or more servers local to the medical care facility 110. Such storage may enable the medical care facility 110 to retain locally medical-related data pertaining to its own patients prior to (or in conjunction with) the medical-related data being shared with the transformative integration engine 102 and/or the transaction management engine 104. In some examples, the one or more servers of the medical care facility 110 share medical-related data directly with a record service (not shown), and the record service makes the medical-related data available to the transformative integration engine 102 and/or the transaction management engine 104. Once an electronic medical record is updated at the medical care facility 110, an indication of the update may be provide to the record service. The record service may then update a corresponding record associated with the electronic medical record.

The record service can be granted access to the medical-related data generated and/or transmitted by the one or more components 106. In some examples, the record service includes a server or a plurality of servers arranged in a cluster or the like. These server(s) of the record service can process and/or store medical-related data generated by the one or more components 106. For example, one or more records can be generated for each patient (e.g., each record corresponding to a different entity or being shared across entities). Upon receiving a communication with medical-related data from an component (or medical care facility), the record service can identify a corresponding record and update the record to include the medical-related data (or processed version thereof). In some examples, the record service provides medical-related data to the transformative integration engine 102.

The medical care facility 110 is a facility at which care is provided to patients. Irrespective of the type of medical care facility, the medical care facility 110 may treat patients, update medical-related data, maintain medical-related data, and communicate medical-related data to the transformative integration engine 102. At least some of the medical-related data may be stored local to the medical care facility 110. Further, the one or more components 106 within the medical care facility can generate medical-related data including administrative information, clinical information, and financial information as part their operations within the urgent care facility. Examples of medical care facilities include, for example, urgent care facilities, outpatient facilities, hospitals, clinics, and other suitable facilities at which care is provided to patients.

The medical care facility 110 is an urgent care facility, an insta-care facility, an emergency room, or the like. For example, a doctor may update a particular electronic medical record of a patient using one of the one or more components 106 or one of the one or more user devices 108 after receiving the patient in the course of an emergency. In some examples, the urgent care facility may be distinct from an office of the patient's primary care provider. However, in accordance with techniques described herein, the updates to the electronic medical record may be made available to the patient's primary care provider, including any medical-care professionals. The update can also be saved locally in association with the patient's electronic medical record, a copy (or the original) can be provided to the transformative integration engine 102, and an indication of the update can be provided to the transaction management engine 104. In some examples, the indication of the update is generated by the transaction management engine 104 as the update is provided to the transformative integration engine 102.

The medical care facility 110 can be an outpatient facility (e.g., a long-term care facility, a recovery facility, a hospice facility, a rehabilitation center, a retirement home, or the like). Such a facility may In some examples, the outpatient facility provide medical care to patients who are not admitted to a hospital. Additionally, components within the outpatient facility generate medical-related data (e.g., administrative information, clinical information, and financial information) as part their operations within the outpatient facility. For example, an outpatient facility may provide treatment to a patient using a dialysis machine. Information pertaining to the treatment of the patient using the dialysis machine can be stored locally, and a copy can then be provided to the transformative integration engine 102 such that it can coordinate storage and later retrieval of the information for use by one or more others of the one or more components 106 of the one or more user devices 108. In addition, an indication of the update to the medical-related data is provided to the transaction management engine 104 (e.g., directly or via transformative integration engine 102). The record service can also maintain updated medical-related data including electronic health record information from the outpatient facility.

The medical care facility 110 can be a hospital (e.g., a type of medical care facility that provides medical, surgical, and other types of medical and nursing care). In this example, the hospital includes one or more different wards dedicated to the care and treatment of patients with particular diseases, disorders, and the like. Within the wards, the hospital includes a variety of different components capable of generating medical-related data. The hospital can store a portion of the generated medical-related data for its own patients locally. In some examples, users (e.g., patients, doctors, etc.) may utilize the one or more components 106 and/or the one or more user devices 108 to generate such medical-related data. For example, the hospital may include, as one of its components, an MRI machine. A technician (e.g., a user) may collect one or more MRI images of a patient using the MRI machine at the hospital. These MRI images, a form of medical-related data, can be stored locally, and a copy of the file can be provided to the transformative integration engine 102, which can coordinate storage and later retrieval of the information for use by one or more others of the one or more components 106 of the one or more user devices 108.

In addition, an indication of the medical-related data can be directly or indirectly provided to the transaction management engine 104. Components of the hospital can also or alternatively communicate the medical-related data to the transformative integration engine 102 or the record service.

In this manner, the transformative integration engine 102 has access to updated medical-related data for the patients of the hospital.

The medical care facility 110 can be a clinic (e.g., an organization of medical care professionals that provide routine medical care). In this example, the treatment offered by the clinic is devoted primarily to outpatients. The clinic offers medical services options to populations in local communities and, in some examples, provides medical services to patients prior to the hospital providing medical services.

The medical provider network 100 includes the one or more components 106 and the one or more user devices 108. One or more users (not shown) can access the components 106 and the user devices 108 to generate, provide, and access medical-related data within the medical provider network 100. In some examples, the medical-related data may have been received by the transformative integration engine 102 and retained for use by others of the components 106 and/or the user devices 108. The one or more users can include, for example, first responders, medical care professionals, patients, or any other suitable type of user.

The first responder can include, for example, an emergency medical technician, a firefighter, a police officer, a member of the military, a designated medical volunteer, and the like. In the context of this specification, the first responder is typically dispatched or directed to the scene of an accident in order to provide medical support to victims.

In some examples, the first responder provides medical-related data to the transformative integration engine 102 using one of the one or more user devices 108 as part of responding to the dispatch. For example, in one example, the first responder arrives at a car accident, identifies a victim by one more means of identification (e.g., a driver's license number, name, address, etc.), and shares the identifying information with the transformative integration engine 102 via one of the one or more user devices 108 (e.g., a mobile phone, a radio, or other communication device). In return, the transformative integration engine 102 can facilitate the provision of medical-related data associated with the victim to the first responder. In this manner, the first responder can be informed of, for example, the medical history and other considerations while providing medical treatment to the victim.

The first responder can provide and/or receive the medical-related data via the one or more user devices 108. Thus, at least in this example, the one or more user devices 108 may operate according to a private and/or proprietary network or protocols. In other examples, the one or more user devices 108 may operate on public networks. In any case, however, the transformative integration engine 102 can have access to the one or more components and can communicate with them via a public, private and/or proprietary network or protocols. The use of one or more private and/or proprietary protocols can promote secure transfer of medical-related data.

In some examples, the one or more users can include a medical care professional and/or care provider. The medical care professional and/or care provider can provide one or more medical-related services, including, for example, examination, surgery, diagnosis, consultation, counseling, scheduling of visits, handling of protected health record information, payment handling, coordination of care, management of care, and the like. In some examples, the medical care professional is associated with the medical care facility 110. In some examples, the medical care professional is a doctor, a nurse, a surgeon, a physical therapist, a medical assistant, or any other person who utilizes medical-related data for treatment of patients. In this example, the medical care professional utilizes some of the one or more user devices 108 to send medical-related data to, and/or receive from, the transformative integration engine 102, medical-related data. In this manner, the medical care professional can receive updates, statuses, progress, and the like relating to patients.

In some examples, the one or more users can include a patient. The patient can be a patient of the medical care facility 110, the first responder, and/or the medical care professional. The patient can include one that has expressly or implicitly authorized the medical care facility 110, the first responder and/or the medical care professional to access and record medical-related data pertaining to services provided to the patient.

Figure 2:
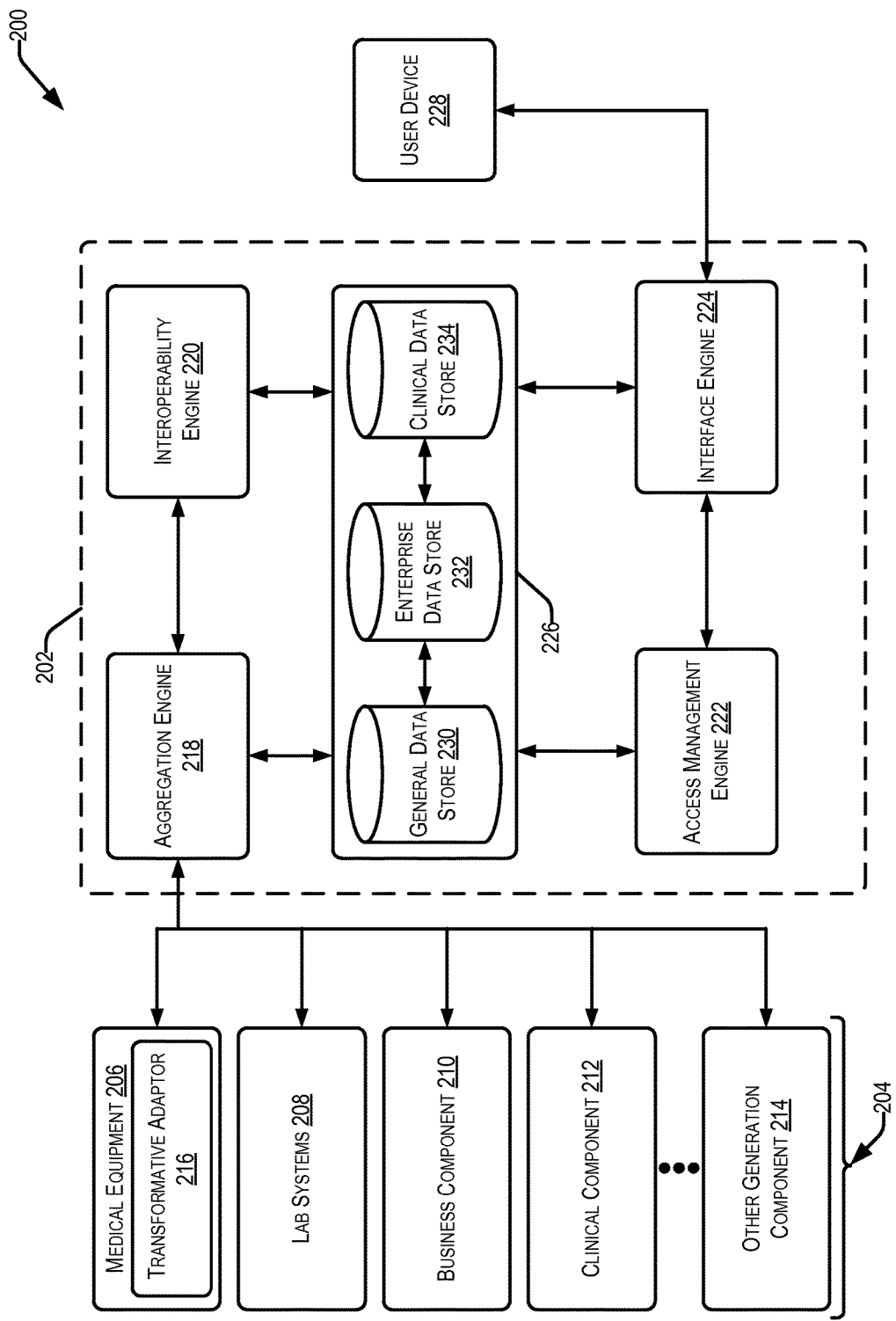
FIG. 2 illustrates a block diagram of an example of a medical provider network, in accordance with certain embodiments of the present disclosure.

Referring next to FIG. 2, a block diagram of an example of a medical provider network 200 is shown. The medical provider network 200 includes a transformative integration engine 202. The transformative integration engine 202 is an example of the transformative integration engine 102 discussed with reference to FIG. 1. The medical provider network 200 also includes one or more generation components 204. In particular, the one or more generation components 204 includes a medical equipment component 206, a lab systems component 208, a business component 210, a clinical component 212, and other generation component 214. The one or more generation components 204 are examples of the one or more components 106 discussed with reference to FIG. 1.

Generally, the one or more generation components 204 includes any suitable device or system capable of generating medical-related data in the context of a medical provider network. For example, the other generation component 214 may include a sensor on a door in a hospital, and the medical equipment component 206 may include a sophisticated computer-controlled laser surgery device. In either case, each generation component generates some type of medical-related data. For example, the medical-related data provided by the sensor may be used to address security concerns or assessing heating, ventilating, and air conditioning (HVAC) costs for the hospital. The medical-related data provided by the laser surgery device may have been provided while operating on a patient and may then be used by other doctors in the future to decide how to use the device on their own patients.

As discussed in further detail herein, medical-related data generated by the one or more generation components 204 can be of a variety of formats, some of which may be proprietary. For example, a single component can generate data in multiple formats, different components can generate data in different formats, and/or different component types can result in generation of data in different formats. In some instances, formatting of a data can depend on a service having been provided, a user initiating data generation, a destination to receive the data, a location at which a service was provided, etc. In some examples, a typical medical provider network includes thousands of generation components producing data in hundreds of formats. In order to harness the power that comes from such a large amount of medical-related data to make informed health care decisions, it is desirable that all, or at least a large portion of the data, is shared. Use of the transformative integration engine 202 in accordance with techniques described herein may achieve this design—making large amounts of data, in many different originating formats available to doctors, nurses, patients, administrators, and third parties, via one or more interfaces.

While the one or more generation components 204 are illustrated adjacent to each other, it is understood that each may be located within one facility or that the components may be spread out among many facilities. In addition, in some examples, the one or more generation components 204 belong to different medical provider organizations.

Turning now to the medical equipment component 206, this component includes any medical machine, contrivance, implant, or other similar related article, that is intended to aid in the diagnosis, monitoring, or treatment of medical conditions. This includes, for example, diagnostic equipment, including medical imaging machines (e.g., ultrasound machines, magnetic resonance imaging (MRI) machines, positron emission tomography (PET) scanners, computed tomography (CT) scanners, and x-ray machines); therapeutic equipment (e.g., infusion pumps, medical lasers, and laser-assisted in situ Keratomileusis (LASIK) lasers); life support equipment (e.g., medical ventilators, anesthetic machines, heart-lung machines, extracorporeal membrane oxygenation (ECMO) machines, and dialysis machines) and/or medical monitors to measure patient's medical state (e.g., electrocardiography (ECG), electroencephalography (EEG), blood pressure machines, and equipment for monitoring dissolved gases in the blood). Each of the above-listed components generates medical-related data that is provided to the transformative integration engine 202.

As illustrated, the medical equipment component 206 includes transformative adaptor 216. In some examples, the transformative adaptor 216 is a device that transforms, translates, converts, or otherwise adjusts output data from the medical equipment component 206. For example, a medical equipment component 206 can be a CT scanner that outputs its results in format A, but the majority of other CT scanners in the medical provider network output their results in format B. The transformative adaptor 216 may be implemented to convert or otherwise adjust the results in format A to conform closer to format B. For example, the conversion from format A to format B may be performed using a conversion rule, which may be user-define or learned. The transformative integration engine 202 may perform similar tasks as it relates to all data generated within the medical provider network 200. In this manner, the transformative adaptor 216 can perform an initial step in the process of transformation, translation, conversion, or adjustment of the output of the medical equipment component 206. In some examples, the transformative adaptor 216 is implemented in hardware, software, or any suitable combination of both. In some examples, other transformative adaptors (not shown) may be implemented within others of the one or more generation components 204. In some examples, the medical equipment component 206 may not include the transformative adaptor 216.

The lab systems component 208 includes any suitable medical laboratory equipment or system that is intended to analyze material related to patient care. This includes, for example, medical laboratory equipment that analyzes blood, urine, and genes; electric microscopes; ultracentrifuges; data collection devices, including Kymographs, sensors connected to a computer to collect data; monitoring devices; computers used by clinicians to report results of lab tests, and other similar medical laboratory equipment. Each of the above-listed components generates medical-related data that is provided (directly or indirectly) to the transformative integration engine 202. The provided data can further include an identification of a patient and/or other patient-pertinent information (e.g., actual or suspected diagnosis and/or demographic information).

The business component 210 includes any suitable computing devices used for business-related purposes with respect to the medical provider network 200. For example, the business component 210 can be configured to receive inputs by employees of a hospital to prepare medical-related data including business-related data relating to eligibility and registration of patients, scheduling and throughputs, general supply chain materials management, pharmacy supply chain materials management, human resources, financial documentation and logging, building operations, information technology systems, marketing, budgeting, and other similar business-related purposes. In some examples, the business-related information is auto-generated or populated by the business component 210. At least a portion of such information is provided to the transformative integration engine 202.

The clinical component 212 includes any suitable computing device used in research, treatment, and care of patients. For example, the clinical component 212 is used to generate medical-related data including clinical data, which may further include an identification of a patient and/or other patient-pertinent information. For example, the clinical component 212 is used by nurses, technicians, doctors, and/or other individuals associated with a hospital, clinic, lab, or other similar entity to prepare clinical data. Clinical data includes, for example, output relating to computerized physician order entry (CPOE), protected health information for patients (i.e., a subset of medical-related data), dictations, lab results, lab requests, lab tests, orders for medical supplies, intake and checkout of patients, medical reports, clinical tests, clinical documentation, and other similar clinical information. At least a portion of such information is provided to the transformative integration engine 202. In some examples, the clinical data is auto-generated or populated by the clinical component 212. The clinical component 212 and the business component 210 are often selected from a similar group of computing devices.

Each of the one or more generation components 204 and the user device 228 may include individual and/or shared storage systems, one or more processors, a user interface, a network connectivity device, and one or more ports. The storage system include memory that may be implemented, e.g., using magnetic storage media, flash memory, other semiconductor memory (e.g., DRAM, SRAM), or any other non-transitory storage medium, or a combination of media, and can include volatile and/or non-volatile media. The storage systems may also be configured to store computer-executable code or instructions for interacting with the user interface and/or for one or more applications programs, such as an application program for collecting medical-related data generated by the particular generation component.

The one or more processors may be configured to access the operating system and application programs stored within the storage systems, and may also be configured to execute such program code. The one or more processors can be implemented as one or more integrated circuits, e.g., one or more single-core or multi-core microprocessors or microcontrollers, examples of which are known in the art. In operation, the one or more processors can control the operation of the particular component. The one or more processors may access and execute the program code and at any given time.

The user interface can include any combination of input and output devices. In some instances, a user can operate input devices of the user interface to invoke the functionality of the particular component or user device. For example, the user interface may enable the user to view, hear, and/or otherwise experience output from component or user device via the output devices of the user interface. Examples of output devices include a display, speakers, and the like.

The network connectivity device may enable the component or user device to communicate with the transformative integration engine 202 and other components or other user devices via one or more networks. The one or more networks may include any suitable combination of cable, cellular, radio, digital subscriber line, or any other suitable network, which may be wired and/or wireless. In some examples, the network connectivity device may enable the component or the user device to communicate wirelessly with various other components and/or the transformative integration engine 202. For example, the components may include circuitry to enable data communication over a wireless medium, e.g., using near-field communication (NFC), Bluetooth Low Energy, Bluetooth® (a family of standards promulgated by Bluetooth SIG, Inc.), Zigbee, Wi-Fi (IEEE 802.11 family standards), or other protocols for wireless data communication.

The one or more ports may enable the component or the user device to receive medical-related data from one or more sensors. For example, a particular port may include an interface for receiving data collected from an ultrasound machine. The sensors may be any suitable type of sensor to capture data. Such captured data may be shared with the transformative integration engine 202 in accordance with techniques described herein. In some examples, the sensors may also be configured to detect the component's or the user device's location and other details about the component or the user device. In some examples, the component and user device may include global positioning chips for determining a geolocation. Such geolocation information may be relevant to analyzing the medical-related data provided by the component or the user device located at the geographic location.

The transformative integration engine 202 includes an aggregation engine 218, an interoperability engine 220, an access management engine 222, an interface engine 224, and a data store 226. Generally the aggregation engine 218 is configured to collect medical-related data of different formats generated by the one or more generation components 204. The aggregation engine 218 may also be configured to perform one or more operations on the collected data. For example, the aggregation engine 218 may tag data, log data, perform protocol conversion, and may support one-to-many communications. The collection may be asynchronous. In some examples, the medical-related data has been saved locally in connection with the one or more generation components 204 in many different formats having many different data structures.

The aggregation engine 218 is configured to receive such diverse (or, in other embodiments, uniformly formatted) data and provide it to the interoperability engine 220. The interoperability engine 220 is configured to perform one or more operations on the received medical-related data and store it in the data store 226. For example, the interoperability engine 220 may perform semantic tagging and indexing of medical-related data. This may include extracting field values from data, categorizing data (e.g., by type of data, characteristic of patient, location of medical care facility, characteristic of medical care facility, and the like), anonymizing or partially-anonymizing data, and the like. The interoperability engine 220 may also include a high availability cache, an alerts engine and a rules engine. In some examples, the interoperability engine 220 operates synchronously.

From the interoperability engine 220, medical-related data flows to the data store 226. The data store 226 (and any other data store discussed herein) may include one or more data stores, which may be distributed throughout two or more different locations (e.g., present on different devices, which can include devices of different entities and/or a cloud server). In some examples, the data store 226 includes a general data store 230, an enterprise data store 232, and a clinical data store 234. Within each of the data stores 230, 232, and 234 is stored medical-related data. Depending on the structure of the particular data store, certain data stores may include rules for reading and writing. The data stores 230, 232, and 234 may include records, tables, arrays, and the like, which may be relational or non-relational. Depending on the data store, records for individual patients, results of clinical studies, business and analytics information, output data from the one or more generation components 204, and the like may be retained. The data within the data stores 230, 232, and 234 include elements or tags such that a particular data (e.g., for a single patient, doctor, diagnosis, type of doctor, type of treatment, patients matching a criteria, and the like) can be retrieved.

The access management engine 222 is configured to manage access to features of transformative integration engine 202, including access to the medical-related data retained in the data store 226. For example, the access management engine 222 may verify that a user device such as user device 228 is authorized to access the data store 226. To verify the user device 228, the access management engine 222 may require that a user of the user device 228 input a username and password, have a profile associated with the medical provider network, have paid a subscription fee associated with access to the data store 226, and the like. The access management engine 222 may also verify that the user device 228 has an IP address or geographical location that corresponds to an authorized list, that the user device 228 includes a plug-in for properly accessing the data store 226, that the user device 228 is running certain applications required to access the data store 226, and the like.

The interface engine 224 is configured to retrieve the data from the data store 226 and provide one or more interfaces for interacting with elements of the transformative integration engine 202. For example, the interface engine 224 includes an interface by which an application running on user device 228 can access portions of data within the data store 226

Figure 3:
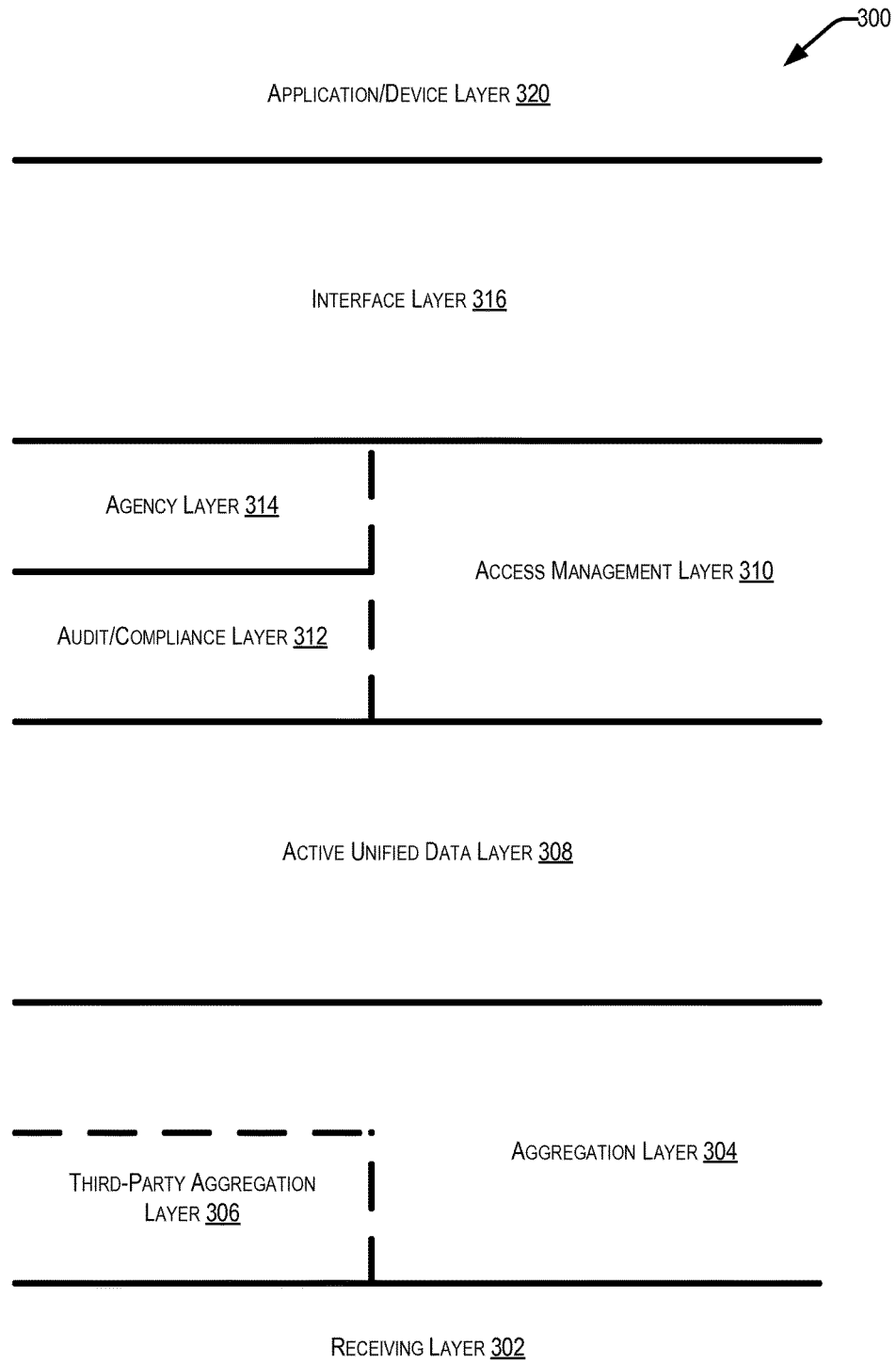
FIG. 3 illustrates a block diagram of an embodiment of a medical architecture stack, in accordance with certain embodiments of the present disclosure.

Turning next to FIG. 3, a medical architecture stack 300 is shown. In some examples, techniques relating management of medical-related data are implemented in accordance with the medical architecture stack 300. And while the medical architecture stack 300 is illustrated as having a particular structure, it is understood that other structures, including those with more or less layers than illustrated, is within the scope of this specification. In some examples, the medical architecture stack 300 is implemented across a medical provider network having a plurality of systems belonging to the same medical provider organization or spread across different medical provider organizations. Thus, the medical architecture stack 300 can be used to integrate different systems of different organizations, entities, and the like and to provide a fluid sharing of information among elements within the medical provider network and without the medical provider network. In some instances, a multi-layer part of the medical architecture stack 300 is implemented at a single system or device within a medical provider network.

The different layers of the medical architecture stack 300 will be described generally with reference to FIG. 3 and in detail with reference to subsequent figures. The medical architecture stack 300 includes a receiving layer 302 as the bottom-most layer. The receiving layer 302 includes receiving medical-related data from elements that share medical-related data with other elements within an aggregation layer 304. For example, as detailed herein, the receiving layer 302 can include receiving medical-related data from generation components that generate medical-related data. As such, the receiving layer 302 is where medical-related data that has been created is received. In some examples, the data within the receiving layer 302 may be in its raw formats. For example, output from an MRI machine may be received within the receiving layer 302. The output may then be transmitted to the aggregation layer 304. In some examples, components of the receiving layer 302 may have complimentary layers to facilitate data transfer. For example, the components may include a data generation and/or a data transmission layer for providing data to the receiving layer 302.

Elements of the aggregation layer 304 aggregate the medical-related data generated by the elements of the receiving layer 302. For example, the elements of the aggregation layer 304 may include aggregation engines that collect data from generation components located within the receiving layer 302. Such aggregation may be performed periodically, in response to a user request, according to a schedule, or in any other suitable manner. In some examples, data of the aggregation layer 304 may be aggregated according to input and/or rules and may aggregate across records pertaining to, e.g., a same medical care professional, medical care facility, entity, time period, patient characteristic (e.g., demographic characteristic or condition), patient health outcome, and any other suitable input and/or rules. Exemplary data being aggregated can include, e.g., diagnosis for particular patients and/or patient groups, test results, treatment parameters or characteristics, health outcomes (e.g., side effect occurrence, mortality, readmissions, sepsis, etc.), pharmacy orders, patient record data, and the like. The aggregation may include compiling the data, generating a distribution, generating a statistic pertaining to the data (e.g., average, median, extremum or variance), converting the data, transforming the data to different formats, and the like.

Next, the medical architecture stack 300 includes an active unified data layer 308. Elements of the active unified data layer 308 receive medical-related data from the elements of the other layers and store such data in a unified manner. In some examples, this may include storing the data in a manner that allows for later searching and retrieval using a defined set of method calls, techniques, and or procedures. For example, the data may be stored such that a different application can access the data in a standard or unified manner. Thus, elements of the active unified data layer 308 may receive information collected or generated within the aggregation layer 304 and make certain adjustments to the data (e.g., translations, tagging, indexing, creation of rules for accessing the data, conversion of formatting of the data, generation of compressed versions, and the like) prior to retaining the data within one or more data stores accessible within the active unified data layer 308.

The medical architecture stack 300 also includes an access management layer 310, which can include an audit/compliance layer 312 and/or an agency layer 314. The access management layer 310 includes elements to manage access to the medical-related data. For example, the access management layer 310 may include elements to verify user login credentials, IP addresses associated with a user device, and the like prior to granting the user access to data stored within the active unified data layer 308.

The audit/compliance layer 312 includes elements to audit other elements of the medical architecture stack 300 and ensure compliance with operating procedures. For example, this may include tracking and monitoring the other elements of the access management layer 310.

The agency layer 314 includes an access location (e.g., a virtual private network, a data feed, or the like) for elements of agencies that are interested in the operations of the medical provider network in which the medical architecture stack 300 is implemented. For example, the agency layer 314 may allow a governmental entity access to some elements within the medical architecture stack 300. This may be achieved by providing the governmental entity a direct conduit (perhaps by a virtual private network) to the elements of the access management layer 310 and the medical-related data within the active unified data layer 308. The audit/compliance layer 312 and the agency layer 314 are sub-layers of the access management layer 310.

The medical architecture stack 300 also includes interface layer 316. The interface layer 316 provides interfaces for users to interact with the other elements of the medical architecture stack 300. For example, medical care providers, patients, medical care administrators, and others belonging to the medical provider network may utilize one or more user devices (interacting within the application/device layer 320) to access the medical-related data stored within the active unified data layer 308. In some examples, the users may be unrelated to the medical provider network (e.g., ordinary users who are not patients, family members of patients, research universities, for profit and non-profit research organizations, world health care organizations, disaster relief organizations, and the like) and may use applications (not shown) to access the elements within the medical architecture stack 300 via one or more interfaces (e.g., to access medical-related data stored within the active unified data layer 308). Such applications may have been developed by the medical provider network or by third-parties.

Finally, the medical architecture stack 300 includes application/device layer 320. The application/device layer 320 includes user devices and applications for interacting with the other elements of the medical architecture stack 300 via the elements of the interface layer 316. For example, the applications may be web-based applications, patient portals, doctor portals, mobile applications, widgets, and the like for accessing the medical-related data. These applications may run on one or more user devices. The user devices may be any suitable user device as detailed herein.

Figure 4:
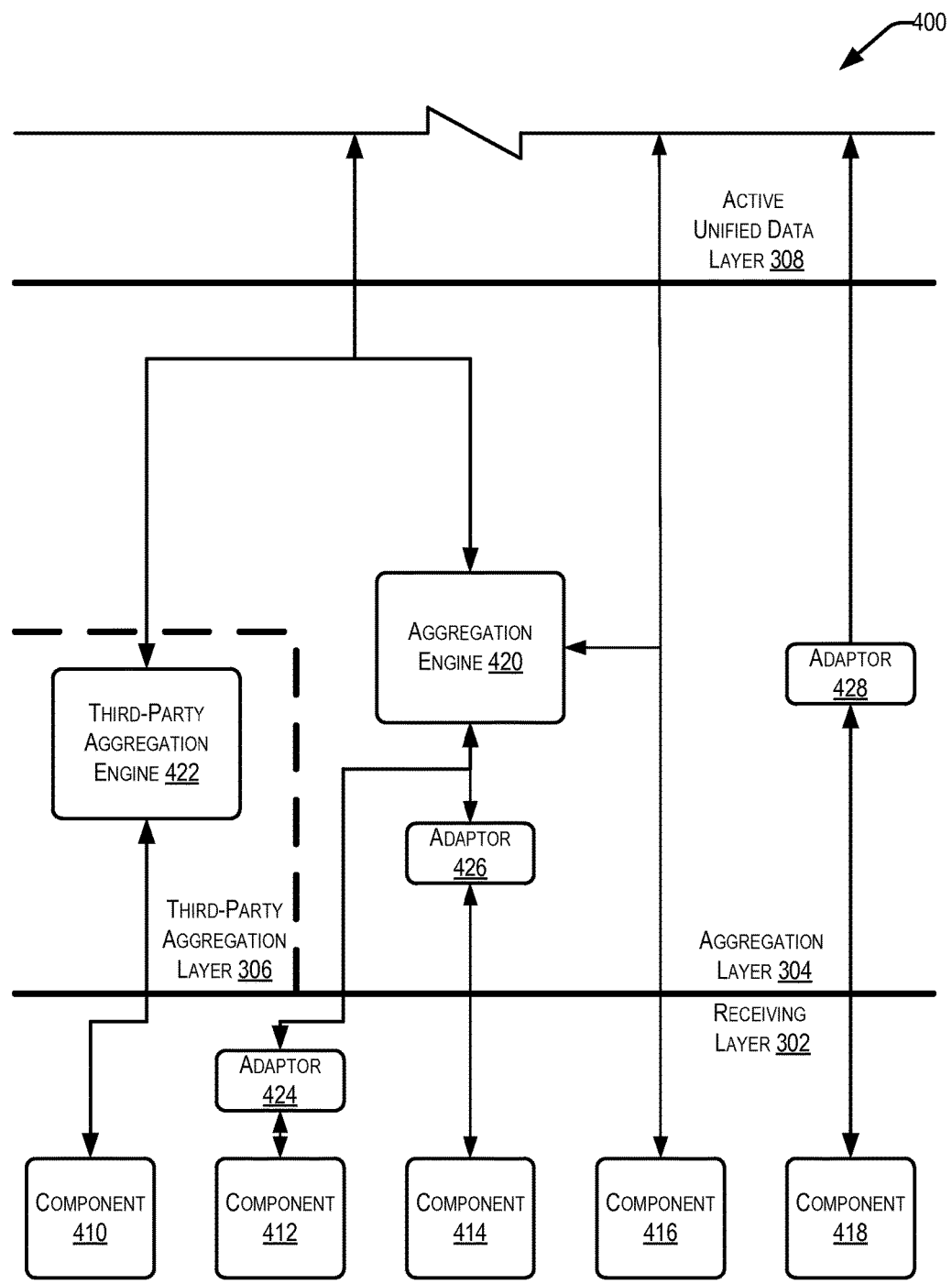
FIG. 4 illustrates a block diagram that depicts a portion of an embodiment of the medical architecture stack, in accordance with certain embodiments of the present disclosure.

Turning next to FIG. 4, a diagram 400 is shown that depicts a portion of the medical architecture stack 300 according to an embodiment of the invention. In particular, the diagram 400 includes the receiving layer 302, the aggregation layer 304, the third-party aggregation layer 306, and a portion of the active unified data layer 308. The receiving layer 302 receives data from one or more components 410-418. The components 410-418 are examples of the one or more generation components 204. The components 410-418 may be spread across multiple medical care facilities within a single or multiple medical provider organizations. For example, the component 410 may be located at a hospital, the component 412 may be located at a clinic, the component 414 may be located at urgent care facility, and so forth. Additionally, the hospital may belong to a first medical provider organization, while the clinic may belong to a second medical provider organization, both of which or part of which may belong to the same medical provider network. In some examples, the components 410-418 may include complimentary layers to facilitate data transmission. For example, the components 410-418 may include a transmission layer, generation layer, and/or a receiving layer to communicate data at the receiving layer 302 and, in some examples, receive data from the receiving layer 302.

In some instances, two or more of the components 410-418 generate medical-related data according to different formats. The medical-related data can then be transformed, translated, or otherwise adjusted before an aggregation engine 420 (e.g., the aggregation engine 218) or a third-party aggregation engine 422 (e.g., the aggregation engine 218) collects the medical-related data. In some examples, the adjustment takes place within the receiving layer 302. Thus, an adaptor 424 is associated with the component 412 located in the receiving layer 302. The adaptor 424 is an example of the transformative adaptor 216. The adaptor 424 is implemented, as appropriate, in hardware, software, or any suitable combination of both. For example, the transformative adaptor 216 may be a bolt-on adaptor that adjusts medical-related data as such data leaves the component 412.

Other adaptors, such as adaptor 426 and adaptor 428, are implemented within the aggregation layer 304. These adaptors can function in a similar manner as the adaptor 424. In some examples, the medical-related data provided by the component 414 is transmitted through adaptor 426 prior to being directed to the aggregation engine 420. The medical-related data provided by the component 416 is transmitted through the aggregation layer 304 and/or enters the aggregation engine 420 without having first traveled through an adaptor. The medical-related data provided by the component 418 is transmitted through the aggregation layer 304 and through adaptor 428. In some examples, the component 418 provides for streaming of medical-related data. The medical-related data provided by the component 410 is transmitted directly to the third-party aggregation engine 422.

The aggregation engine 420 and the third-party aggregation engine 422 function in a similar manner. In some examples, the third-party aggregation engine 422 is operated by a different entity than the entity that operates the aggregation engine 420 and may belong to different medical provider organizations or a different medical provider network. This may be because the medical-related data collected by the third-party aggregation engine 422 differs in some way from the medical-related data collected by the aggregation engine 420. In any event, the aggregation engine 420 is configured to perform integration of medical-related data, including generic integration. For example, the aggregation engine 420 performs one or more operations on medical-related data including tagging, logging, and protocol conversion. The aggregation engine 420 also supports one-to-many communications of medical-related data. In some examples, medical-related data flows between the aggregation engine 420, the third-party aggregation engine 422, and some of the components 410-418 and elements of the active unified data layer 308.

Figure 5:
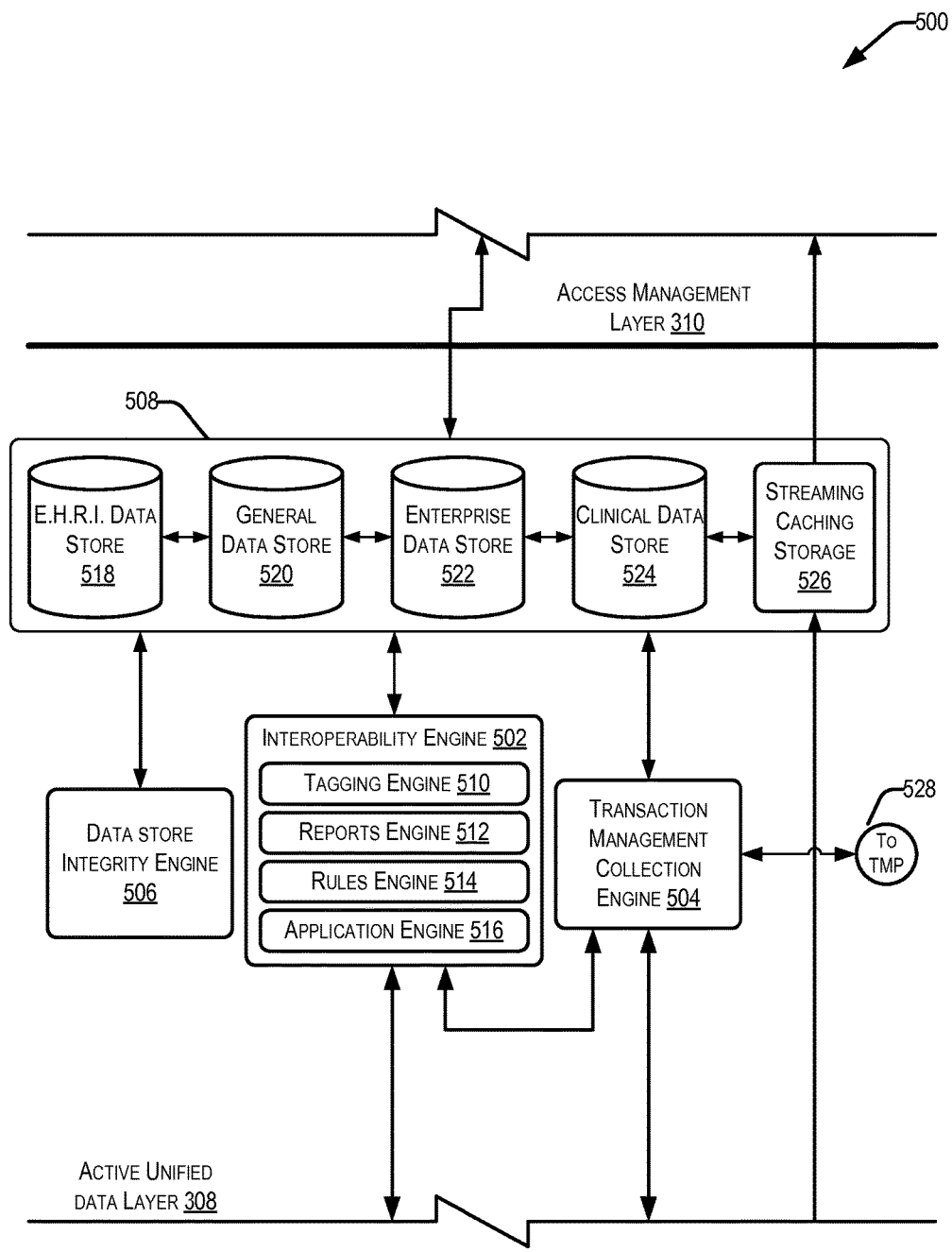
FIG. 5 illustrates a block diagram that depicts a portion of an embodiment of the medical architecture stack, in accordance with certain embodiments of the present disclosure.

Referring next to FIG. 5, a diagram 500 is shown that depicts a portion of the medical architecture stack 300 according to an embodiment of the invention. In particular, the diagram 500 includes the active unified data layer 308 and a portion of the access management layer 310. The active unified data layer 308, as illustrated in the diagram 500, includes an interoperability engine 502 (e.g., the interoperability engine 220), a transaction management collection engine 504, a data store integrity engine 506, and a data store 508 (e.g., the data store 226). Generally, the interoperability engine 502 receives medical-related data from elements within the aggregation layer 304 (e.g., from the aggregation engine 420) and performs one or more operations with respect to the medical-related data. The interoperability engine 502 also facilitates storage of at least a portion of the processed information in the data store 508.

The transaction management collection engine 504 is implemented as part of the transaction management engine 104. The transaction management collection engine 504 is configured to generate message indicators identifying flows of data by and between elements of a medical provider network implemented using the techniques described herein. The flows of information include messages which include medical-related data, and the message indicators include unique message identifiers that can be used to identify the messages. The unique message identifiers include information that can be used to uniquely identify the messages. For example, a unique message identifier for a particular message can include a concatenation of the following information stored in a table: a source application, a facility, a message type, and a message control identification (ID). The unique message identifier can also be the message control ID. The unique message identifier may be created as messages including medical-related data are transmitted from the aggregation layer 304. The table may be stored in association with the transaction management platform 528.

In some examples, the table also includes information for tracking the progress of the message from an origination node to a destination node. For example, typically when a message (e.g., any communication of data) is first received by the transformative integration engine 102 (e.g., the interoperability engine 502), the transaction management engine 104 (e.g., the transaction management collection engine 504 of the transaction management engine 104) may generate a unique identifier for the message in order to track that message as it moves throughout the medical provider network. The unique identifier may be included in the header of the message such that when the next node (e.g., component, device, server, etc.) after the transformative integration engine 102 receives the message, that node can report back to the transaction management engine 104 that it saw the message. In this manner, the transaction management engine 104 may enable end-to-end tracking of messages for the life of the message. In one example, the messages are pharmacy orders. The pharmacy orders may be generated by a user entering in the orders at one of the components. The orders may be received by the transformative integration engine 102 and integrated into the system. In some examples, the transaction management engine 104 may be notified that the orders have been received and may therefore be configured to generate message IDs for each order. These message IDs may then be associated with each of the orders. As the orders continue to move throughout the medical provider network (e.g., away from the transformative integration engine 102), the transaction management engine 104 may be track their movement using the message IDs. If one of the orders does not make it to its destination, the transaction management engine 104 (or part of the transaction management platform 528) may determine why the order was stopped. In some examples, this cause may be hardware related (e.g., an unplugged Ethernet cable, a broken router, etc.), software related (e.g., a router routing to the wrong location), or any other reason for orders not arriving at their correct destination.

In some examples, the transaction management engine 104 (e.g., the transaction management collection engine 504 of the transaction management engine 104) may receive the message and/or message identifier directly from one of the components 410-418. For example, one of the components 410-416 may be configured to generate the unique message identifier and/or communicate directly with the transaction management engine 104. The message also may travel via one or more intermediate odes on its way to the destination node. In some examples, a node is a component such as the components 410-418, which may be running an application. In some examples, the unique identifier and the routing of the message to its destination may be stored in a table that also includes: a geolocation of each node, a network from which the message originated, a type of node, the unique node identifier, and a time associated with the message leaving the origination node. In some examples, the transaction management collection engine 504 provides unique message identifiers to other elements of the medical provider network to monitor the messages as they move throughout the medical provider network. The transaction management collection engine 504 also provides a portion of the unique message identifiers to a transaction management platform (indicated by circle 528) for further analysis of the message identifiers. Such analysis may include reconciliation of lost messages, latency reporting, audit management and compliance, and other such analyses.

As mentioned previously, the interoperability engine 502 is configured to store medical-related data in the data store 508. A plurality of sub-engines 510-516 of the interoperability engine 502 are configured to perform operations relating to storing medical-related data in the data store 508.

The interoperability engine 502 includes a tagging engine 510 configured to perform semantic tagging and indexing of medical-related data. The tagging engine 510 therefore is configured to receive medical-related data, read metadata associated with the medical-related data, semantically scan the content of the medical-related data, and associate one or more tags with the medical-related data. The tagging engine 510 may therefore have access to hundreds, thousands, or even more possible tags. These tags may have been input by users, learned, pre-defined, and/or gathered from other components and/or data stores of the medical provider network. For example, if the medical-related data is a medical chart for a cancer patient, the tagging engine may be configured to read any metadata associated with the chart to determine which tags may be appropriate to associate with the chart. From the metadata the tagging engine 510 may determine that the chart is for a cancer patient by reading metadata indicating that an author field is populated with the name of an oncologist who prepared the medical chart. The tagging engine 510 may have access to other data to compare the analyzed metadata against (e.g., to identify that the author's name corresponds to Dr. Brown who is an oncologist). Other examples, of metadata that may be included in one or more fields include author, document type, creation time and date, last update time and date, upload time and data, geographic location, unique ID associated with the medical care provider or medical care facility where the data originated, and other similar fields. The tags may be stored in association with the medical-related data (e.g., the chart) and/or may be stored independent from the medical-related data but include an identifier such that when searching tags the medical-related data may be capable of population.

Continuing with the example from above, if the medical-related data is a medical chart for a cancer patient, the tagging engine 510 may be configured to read the content of the chart to determine which tags may be appropriate to associate with the chart. For example, this may comprise analyzing the content of the chart (i.e., individual pages) semantically to look for artifacts (e.g., keywords, phrases, and the like) in the content. These artifacts may be identified by the tagging engine 510 and used to decide which tags to associate with the document. In some examples, semantic scanning may involve filtering out words (e.g., articles, such as "a" and "the"), phrases, and the like. Similar to the reading of metadata, the tags may be pre-defined, user-defined, learned, and the like. In some examples, reading metadata associated with messages may provide meaning and/or give context to the particular record of medical-related data. This meaning and/or context may assist the tagging engine 510 to determine one or more tags to associate with the medical-related data. The tags may be chosen, for example, based on values of particular fields in the data, detecting a frequency of one or more words in a document or metadata and/or of a set of related words (e.g., tagging a record with "cancer" upon detecting words such as tumor, metastasize, chemotherapy, radiation, oncology, malignant, stage 3, etc.). In this manner, the tagging engine 510 may also index portions of the medical-related data within one or more data stores of the data store 508. In some examples, the such indexing may be based in part on the selected tags.

The interoperability engine 502 also includes an reports engine 512 configured to generate one or more reports or alerts based on medical-related data. For example, the reports engine 512 may generate reports when certain types of medical-related data are received or when medical-related data with certain characteristics is received. The reports engine 512 may also generate alerts. The reports and/or alerts generated by the reports engine 512 may be outputted in the form of one or more communications to an administrator, an authorized user, or other similar user via a user device. Such communications include, for example, signals, sirens, electronic notifications, popups, emails, and the like. Content of such communications may include information characterizing a care provider's or institution's performance in providing care, efficiency and/or patient outcomes; identifying concern patient-data patterns; identifying losses of medical-related data; and the like. In some examples, the content is presented in the form of one or more documents, tables, figures, charts, graphs, and the like. For example, the reports engine 512 may output a report to a hospital administrator indicating the patient outcomes for the hospital for the last year. This report may be presented in the form of a graph.

The interoperability engine 502 also includes a rules engine 514 configured to create and manage business rules, health-response rules, alert/reports rules, data-formatting rules, data-sharing rules, transmission rules, aggregation rules, user authorization rules, law-based rules, and other similar rules. Such rules may be user-defined, fixed, learned by elements of the medical provider network, and any combination of the foregoing. For example, a business rule may be defined by a hospital administrator and relate to supply chain management and visualization and optimization of planning and scheduling. The rules can apply across different medical care facilities, medical conditions, patient types, geographic areas, and/or entities. Finally, the interoperability engine 502 includes an application engine 516 configured to provide service-oriented architecture web services.

The data store 508 includes an electronic health record information (EHRI) data store 518 ("the record data store 518"), a general data store 520, an enterprise data store 522, a clinical data store 524, and a streaming caching storage 526. While the data store 508 is illustrated as including a fixed number of data stores and storage elements, it is understood that the data store 508 can include any suitable number of data stores and storage elements, including more than illustrated or less than illustrated.

In some examples, a data query script is provided to query a first data store and/or to obtain data for populating a data store. Such script could query a data store described herein (e.g., data store 508) and/or could be used to obtain data to populate a data store described herein (e.g., data store 508). In one instance, the script is configured to be repeatedly executed, so as to repeatedly draw data from a source data store. The retrieved data can then be formatted, filtered, sorted and/or processed and then stored, presented and/or otherwise used. In this manner, the script can be used to produce streaming analytics.

In some instances, the data query script, when executed, identifies each of the data stores of interest. Identifying the data stores of interest involves identifying at least a portion of data from the data stores simultaneously and/or sequentially. For example, the script can identify corresponding data stores (e.g., or components of a single data store or multiple data stores) that pertain to one or more similar variables (e.g., pertaining to a similar medical condition, treatment, physician or geographical region) but that differ in one or more other variables (e.g., institution affiliation). Once the portion of the data from the data stores is identified, a representation of the identified data can be output to one or more files (e.g., Extensible Markup Language (XML) files) and/or in one or more formats. Such outputs can then be used to access the data within one or more relational database accessible using Structured Query Language (SQL). Queries made using SQL can be made sequentially or in parallel. Results from an SQL query may be stored in a separate database or in an XML file that may be updated either in part or as a whole. The data query script may be executed periodically, in accordance with a user-defined rule, in accordance with a machine-defined or machine-learned rule, and in other suitable manner.

Within the record data store 518 is retained medical-related data including electronic health record information. In some examples, the information within the record data store 518 is organized according to patient identifying information. Thus, the record data store 518, in some examples, includes individually identifiable information. But it may also include de-identified information.

Within the general data store 520 is retained medical-related data in a relational database format. Thus, the data within the general data store 520 may be retained in a data structure that includes one or more tables capable of accessing each other. The general data store 520 includes certain types of clinical information. For example, the general data store 520 may include orderables and labs.

Within the enterprise data store 522 is retained medical-related data in a relational database format. Thus, the data within the enterprise data store 522 may be retained in a data structure that includes one or more data structures (e.g., tables) capable of accessing each other. The enterprise data store 522 is an example of an enterprise data warehouse. In the enterprise data store 522 is joined many different types of medical-related data. For example, clinical, financial, and administrative information are stored in the enterprise data store 522.

Within the clinical data store 524 is retained medical-related data in a non-relational database format. Thus, the data within the clinical data store 524 may be retained in a structure other than tables. Such structure may be appropriate for large and complex data sets including medical-related data. In some examples, the clinical data store 524 (or any other data store) may be a unified system for clinical information, which may include: a document-centric, schema-agnostic, structure-aware, clustered, transactional, secure, database server with built-in search and a full suite of application services. An example of such a unified system may be Marklogic. The clinical data store 524 can support data aggregation, data organization, data indexing, data tagging and mapping to semantic standards, concept matching, concept extraction, machine learning algorithms, concept discovery, concept mining, and transformation of personal medical record information.

Finally, in some examples, the streaming caching storage 526 is a streaming data cache data store. As discussed previously, certain components of the components 410-418 may support streaming data to other components or user devices. The streaming caching storage 526 is a location where streaming data can be cached. For example, assume that the component 418 is an MRI machine operated by a technician in hospital A and that a doctor using a computer in hospital B desires to view a live of substantially live stream of the MRI results. The component 418 can send a portion of data to the streaming caching storage 526 which can retain the portion of the data for a certain period of time (e.g., 1 day). Thus, the streaming caching storage 526 is configured to cache data that can be streamed.

The diagram 500 also includes data store integrity engine 506. In some examples, the data store integrity engine 506 is configured to ensure integrity of the information within the data store 508. For example, the data store integrity engine 506 applies one or more rules to decide whether information within all or part of the data store 508 should be scrubbed, removed, or adjusted. In this manner, confidence is increased that the information within the data store 508 is accurate and current.

Figure 6:
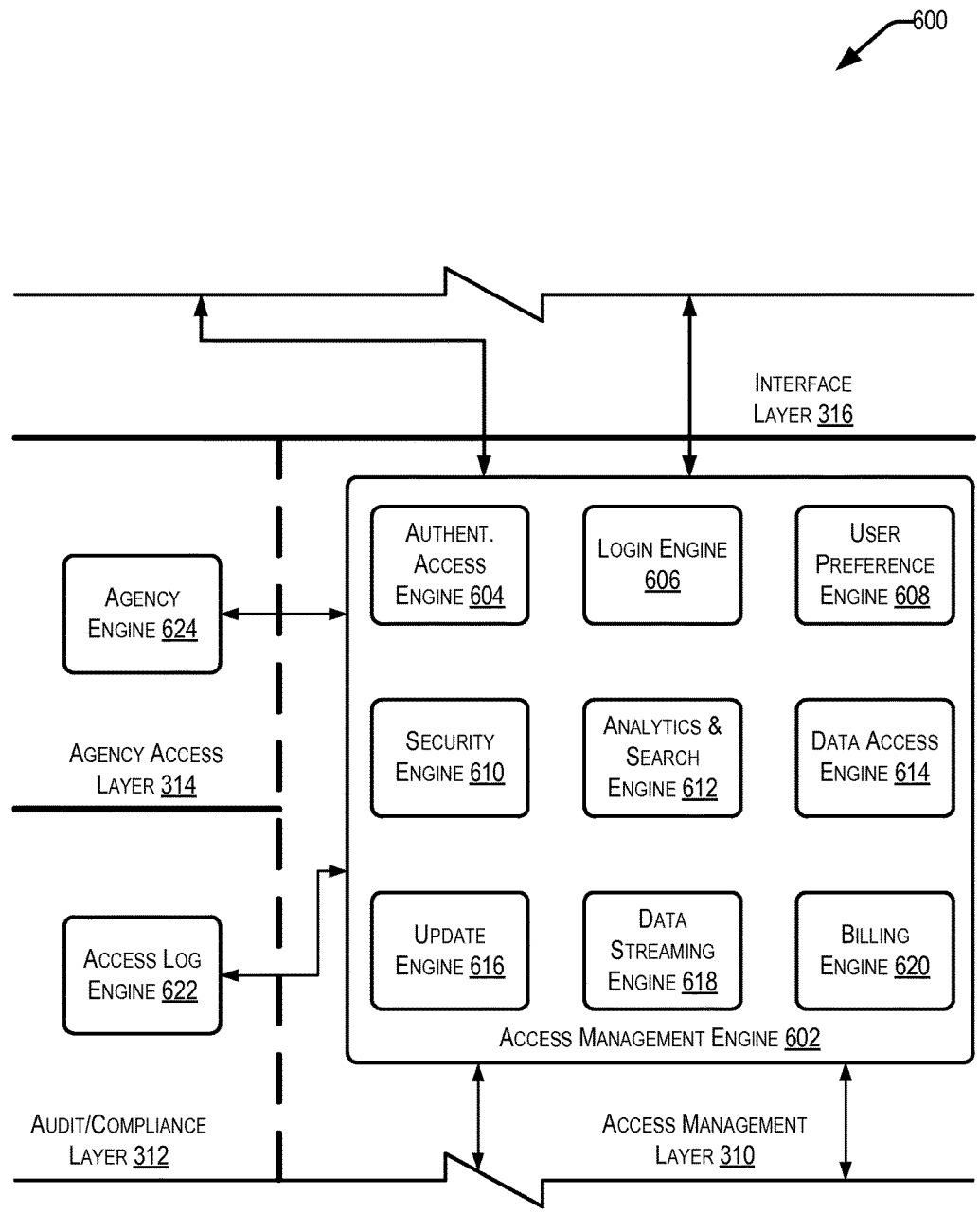
FIG. 6 illustrates a block diagram that depicts a portion of an embodiment of the architecture stack, in accordance with certain embodiments of the present disclosure.

FIG. 6 shows a diagram 600 which depicts a portion of the medical architecture stack 300 according to an embodiment of the invention. In particular, the diagram 600 includes the access management layer 310, the audit/compliance layer 312, the agency layer 314, and a portion of the interface layer 316.

The access management layer 310, as illustrated in the diagram 600, includes an access management engine 602. The access management engine 602 is an example of the access management engine 222. Generally, the access management engine 602 can be configured to manage access to elements of the transformative integration engine 202 by different components, applications, and user devices.

The access management engine 602 within the access management layer 310 also provides functionality similar to an operating system. For example, the access management engine 602 includes a plurality of engines configured to manage different aspects of interacting with elements of the medical provider network. For example, a user who desires to access portions of medical-related data retained in the data store 508, may do so by interacting with the access management engine 602 using one or more applications (not shown). Thus, the access management engine 602 includes a variety of engines to enable such interaction. The engines include, for example, an authentication access engine 604, a login engine 606, a user preference engine 608, a security engine 610, an analytics and search engine 612, a data access engine 614, an update engine 616, a streaming data engine 618, and a billing engine 620. The different engines of the access management engine 602 can define routines, protocols, standards, and the like for interacting with elements of the medical provider network.

Beginning first with the authentication access engine 604, the authentication access engine 604 evaluates the rules and conditions under which users may access elements of the medical provider network; in particular, the conditions under which users may access medical-related data within the data store 508. These rules and conditions may be user-defined (e.g., by an administrator or reviewer), learned over time, and/or may be dynamically updated and/or evaluated based on characteristics of the user or the user's device attempting to access the medical provider network. The rules and conditions may indicate the types of users who have particular types of access within the medical provider network. For example, hospital administrators may have a different type of access from a patient. The type of access may also relate to the degree to which data is identified/de-identified. For example, a doctor to whom a release has been given, may have access to all of a patient's medical record. Similarly, a researcher may have access to the records for many patients, so long as the records are do not include identifying information. In some examples, a user desiring access to medical-related data provides certain identifying information and the authentication access engine 604 authenticates an identity of the user. For example, suppose the user is a doctor and the access is to medical charts for one of the doctors patients. To authenticate the doctor's identity, he or she provides identifying information and once validated can be granted access to elements of the medical provider network where such information may be stored.

The login engine 606 evaluates the rules and conditions under which users are able to log in to the medical provider network or access applications associated with the medical provider network. These rules and conditions may be user-defined (e.g., by an administrator), learned over time, and also may be dynamically updated and/or evaluated based on characteristics of the user or the user's device attempting to access the medical provider network. Thus, while the authentication access engine 604 evaluates the rules to determine which users may access the medical provider network, the login engine 606 evaluates the particular credentials, profiles, etc. of the users. For example, the login engine 606 can confirm that an entered username (e.g., and password), provided biometric data or code or identifier in a scanned tag or badge matches that in an authorized user data structure.

The login engine 606 evaluates one or more user profiles associated with each authenticated user. In some examples, a user profile includes a username, password, and other information associated with the user. For example, a user profile may indicate characteristics about the user (e.g., that the user is patient belonging to a particular doctor, that the user is an employee belonging to a particular medical care facility, that the user is a vendor seeking access to certain portions of the medical provider network, that the user is a doctor having a particular specialty, that the user is a scheduler who belongs to a clinic, and other characteristics).

The user preference engine 608 evaluates the rules and conditions under which user are able to store and update one or more user preferences corresponding to access of the medical provider network or access to applications associated with the medical provider network. These rules and conditions may be user-defined (e.g., by the user or administrator), and may include rules for default preferences. For example, using the user preference engine 608, a user may indicate a format in which the user prefers to receive outputted information, display characteristics of a graphical user interface associated with the user, and other similar user preference settings. For example, the user may indicate that certain types of reports and/or alerts are to be sent to the user.

The security engine 610 evaluates the rules and conditions for ensuring the security of access to the elements of the medical provider network. In some examples, these rules and conditions are determined by administrators of the medical provider network. In some examples, the security engine 610 provides a plurality of computer virus protection services. These services can be called up and implemented when accessing the medical provider network or accessing applications associated with the medical provider network. The rules and conditions may be based on roles, based on profiles, based on domains, and any other suitable security configuration. For example, because the medical provider network may include sensitive medical-related data, the security engine 610 may enforce a domain-based rule that protects certain sensitive information (e.g., identifying information).

The analytics and search engine 612 evaluates the rules and conditions under which users can search for data within the medical provider network and access analytics relating to the medical provider network. In some examples, these rules and conditions are user-defined or learned over time in accordance with search engine optimization techniques. For example, the analytics and search engine 612 is used to search within the data store 508 for particular medical-related data. The analytics and search engine 612 supports any conventional searching algorithms. For example, the search engine 612 can be used to search within various fields and potential field values (e.g., Hospital field, state field, specialty field, diagnosis field, health outcome field, doctor field). In some examples, search engine 612 can provide analytics, such as statistics, graphs, distributions and/or comparative analysis pertaining to particular entities and/or medical characteristics. Such information may be selected by a user and presented on a user interface.

The data access engine 614 evaluates the rules and conditions under which users may operation in order to access particular medical-related data within the data store 508. In some examples, these rules and conditions are user-defined or learned over time. For example, the data access engine 614 may indicate the routines, subroutines, or other logic needed for an application to access certain portions of the data store 508. For example, while the authentication access engine 604 and the login engine 606 may manage which users can access parts of the medical provider network, the data access engine 614 may manage how authenticated users access data within the data store 508. To this end, the data access engine 614 may enforce and/or evaluate certain rules managing how users access different components of the medical provider network. In some examples, the data access engine 614 may be used to actually access data within the data store 508 (e.g., extract, download, or otherwise access). In some examples, the data access engine 614 may define procedures, protocols, and the like for accessing data. The protocols and procedures for accessing the data access engine 614 (like the other engines of the access management engine 602) may be provided to developers in the form of a software development kit (SDK). SDKs may enable developers write applications that can effectively communicate with elements (e.g., the data store 508) of the medical provider network. In particular, applications that can access a portion of the medical-related data stored within the active unified data layer 308.

The update engine 616 evaluates the rules and conditions for providing updates to other engines within the access management engine 602, plug-ins for applications that access the medical provider network, and for other similar elements of the medical provider network. For example, updates may be generated at runtimes, at defined time intervals, upon request by a user, upon receiving a threshold quantity of new or changed data. Once an update is performed, an interface may be refreshed, a report may be sent indicating that the update was successful or unsuccessful, or the like.

The streaming data engine 618 defines the rules and conditions for enabling streaming of medical-related data between components and user devices of the medical provider network. For example, the streaming data engine 618 may enable the component 414 to stream medical-related data. Streamed data may include live or substantially live audio or video feeds, results of medical tests, output from medical equipment or devices, and any other suitable type of medical-related data capable of being streamed. In some examples, the data may be streamed to other components or user devices within the medical network or outside the medical network. In order to establish a streaming transmission, the streaming data engine 618 may identify a streaming destination and a streaming origin. Next, the streaming data engine 618 may pair the two and enable streaming. This may include allocated bandwidth within one or more network devices associated with the medical provider network. The streaming data engine 618 may also adjust the quality of the streaming data based on the availability of bandwidth. In some examples, the streaming data engine 618 may receive incoming streams (and continuously present the stream or monitor for particular data (e.g., exceeding a threshold, exhibiting an above-threshold change, having a particular value)).

The billing engine 620 evaluates the rules and conditions under which applications and users that access the medical provider network are billed. For example, the billing engine 620 may include a variety of different charging rules to be applied to applications and users. An example rule indicates that applications or users will be charged on an hourly basis, another indicates that applications or users will be charged on a data transfer basis in terms of bytes, and another indicates that the applications or users will be charged a single amount for unlimited use. The billing engine 620 also indicates, not only how applications and users are charged, but also how they billed (e.g., periodically, directly to users, to an organization, etc.). The billing engine 620 may also indicate how medical bills are calculated, compiled, and determined for users of the medical provider services and include the procedures for accessing one's bill. For example, the billing engine 620 may enforce billing structures rules for certain services provided by medical care professionals at medical care facilities. The billing engine 620 may also define the rule under which users (e.g., patients, doctors, nurses, etc.) may access their own bills and bills associated with others. In some examples, this may include stripping away certain protected-health information, identifying information, and the like. The engines of the access management engine 602 are accessed via the interface layer 316 discussed later.

Within the audit/compliance layer 312 is located an access log engine 622. The access log engine 622 evaluates the rules and conditions for logging access to the medical provider network by users, applications, devices, and the like. Logging access includes, in some examples, logging data conventionally collected by access log engines running in similar environments. Access log engine 622 can use this data to generate and transmit reports, for example, to stakeholders of the medical provider network such that they can make informed decisions regarding that is accessing the medical provider network and for what purposes.

Within the agency layer 314 is located an agency engine 624. The agency engine 624 evaluates the rules and conditions under which agencies can access the medical provider network. For example, agencies that may use the agency engine 624 include agencies to which the medical provider network provides compliance, tracking, or other reporting information. For example, the agency engine 624 may be used to track one or more performance indicators identified by a government agency, to report occurrences of infectious diseases, and to provide other similar reporting. Thus, in some examples, a government agency uses the agency engine 624 to collect data pertaining to compliance of the medical provider network with one or more statutes or regulations. In some examples, a university is an agency that uses the agency engine 624 to collect data pertaining to one or more studies. In some examples, the agency engine 624 can identify one or more entities (e.g., governmental agencies) that are to receive reports pertaining to medical operations or events and what types of data are to be reported to those entities. The agency engine 624 can then collect the pertinent data, potentially format and/or analyze the data, and facilitate transmission of (e.g., raw, formatted and/or analysis of) the data to the appropriate agency.

Figure 7:
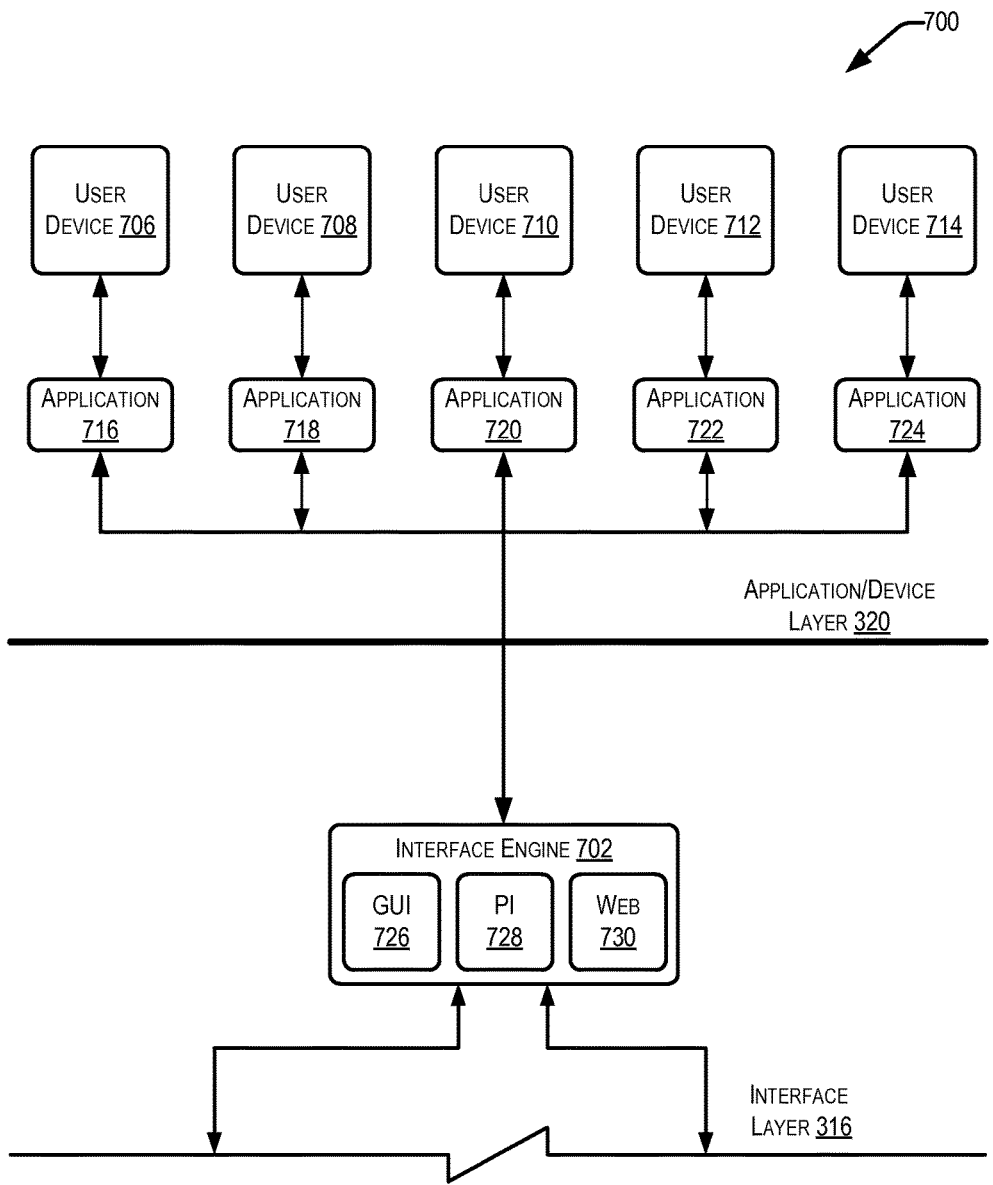
FIG. 7 illustrates a block diagram that depicts a portion of an embodiment of the architecture stack, in accordance with certain embodiments of the present disclosure.

FIG. 7 shows a diagram 700 which depicts a portion of the medical architecture stack 300 according to an embodiment of the invention. In particular, the diagram 700 includes the interface layer 316, and the application/device layer 320. Within the interface layer 316 is located interface engine 702 (e.g., the interface engine 224). The interface engine 702 is configured to generate one or more interfaces (e.g., graphical user interface 726, programmatic interface 728, and/or web interface 730) to enable medical-related data to flow to user devices 710, 712, and 714 via respective applications 720, 722, and 724. In some examples, the interfaces of the interface engine 702 are embodied in hardware, software, or some combination of both. Within the interface layer 316 communications and inputs directed to interacting with elements of the access management layer 310 may be embodied.

The graphical user interface 726 is any suitable graphical user interface configured to interact with elements of the medical provider network. The programmatic interface 728 includes an application programming interface, a programmatic user interface, and other similar interfaces for defining core functions for accessing elements of the medical provider network. For example, the programmatic interface 728 may specify software components in terms of their operations. The web interface 730 is any suitable web interface configured to interact with elements of the medical provider network. Any of the interfaces described herein may be configured to receive user input, present dynamic presentations that depend on user input, and otherwise respond to user input. In some examples, such input may be provided via one or more input devices (e.g., a keyboard, touchscreen, joystick, mouse, microphone, medical devices capable of capturing inputs, and the like) operated by one or more users of the user devices 706-714. Output may be provided via one or more output devices (e.g., a display or speaker).

The interface engine 702 is utilized by applications internal to the medical provider network and external to the medical provider network to access medical-related data. In some examples, the applications that are internal include applications that are developed for internal use by employees, patients, nurses, medical care professionals, medical care providers, contractors, and others associated with the medical provider network. In some examples, the applications that are external to the medical provider network include applications that are developed for external use by those that are not associated with the medical provider network.

Generally, within the application/device layer 320, the applications 716-724 which communicate with other elements of the medical architecture stack 300 using the interfaces generated by the interface engine 702 are defined. This includes detailing how the applications 716-724 are to interact with the interfaces generated by the interface engine 702 for accessing medical-related data. For example, interacting may include accepting inputs at the user devices 706-714 to access medical-related data and, in response, providing the data, prompts, or other types of interaction with one or more users of the user devices 716-714. Thus the applications 716-724 may be related to one or more of the interfaces generated by the interface engine 702. For example, the application 720 may be interact with a graphical user interface (whether generated by the interface engine 702 or otherwise) to interact with other elements of the medical provider network. Interacting may include receiving inputs at the graphical user interface via the application 720, providing output data (e.g., medical-related data including reports, data sets, patient record information, diagnosis information, treatment care information, and the like) to the graphical user interface via the application 720, enabling interaction with other user devices, other applications, and other elements of the medical provider network, and the like. For example, some of the inputs may pertain to aggregation of medical-related data. These inputs may include, for example, types of data to aggregate, aggregation parameters, filters of interested data, keywords of interested data, selections of particular data, inputs relating to presentation of the data on the graphical user interface, and the like. Providing output data may include providing the aggregated data on the graphical user interface, outputting the information to one of the other user devices 706-714 running one of the other applications 716-724.

Turning now to the details of the applications 720, 722, and 724. In some examples, the applications 720, 722, and 724 include a variety of different applications that can be designed for particular users and/or uses. In one example, the application 720 is specific for doctors. In this example, the application 720 includes dashboards, widgets, windows, icons, and the like that are customized to the individual doctor. In some examples, the application 720 may present different medical-related data depending on a specialty associated with the doctor and protected health information associated with the doctor's patient. In this manner, the application 720 adapts and automatically adjusts depending on the context in which the doctor is using the application. In some examples, the medical-related data indicates performance statistics for the doctor, metrics relating to where the doctor falls along a distribution of other similar doctors, outlier patients, trends in diagnosis numbers and release, rapid changes in health-related values for the doctor's patients compared to other similar patients, and the like. The application 720 may be configured to receive input, adjust presentations, present unprompted alerts, adjust display of content, move more relevant content to the foreground, move less relevant content to the background, populate forms for the doctor to order tests, and the like.

In another example, the application 722 may be specific for nurses or types of nurses. In this example, the application 722 may include dashboards, widgets, windows, icons, and the like that are customized to individual nurses. Similar to the example discussed above pertaining to the doctor, in some examples, the application 724 may present different medical-related data depending on a position of the nurse. In this manner, the application 722 adapts and automatically adjusts depending on the context in which the nurse is using the application. For example, the nurse may receive medical-related data, such as test results for a patient.

In some examples, the application 724 may be a multi-role application for administrators and is used to manage patients and others that constitute the population of the entities or organizations within the medical provider network. Similar to the other examples discussed, in some examples, the application 724 may present different medical-related data depending on a role of the user who is using the application 724. In this manner, the application 724 adapts and automatically adjusts depending on characteristics of the user who is using the application 724. In this manner, the application 724 provide different medical-related data depending on the role of the user. For example, to an administrator may be presented identifying or de-identified information that characterizes overall flow of patients within a hospital (e.g., intake date, insurance, bed location, expected checkout date, etc.).

In some examples, the application 724 may be a business intelligence application. In this example, the application 724 is used to display business information generated by components of the medical provider network. This business information can be used for operations, planning, and forecasting. Such business information may include medical-related data because such data may impact operations, planning, forecasting, and the like. Accordingly, the application 724 may present de-identified information in the form of one or more metrics, indicators, or the like as they pertain to business intelligence.

The applications 716 and 718 shown in connection with the interface engine 702 are applications developed by third-parties. In some examples, such applications include any suitable application that benefits from accessing medical-related data. For example, the application 716 may be a health application, a nutrition application, a fitness application, and other similar applications. The medical provider network may include medical-related data pertaining to hundreds of thousands of patients. Having data pertaining to so many patients presents security concerns. For example, much of the medical-related data may be identifying data. Certain disclosure laws may prohibit the disclosure of such information. Accordingly, data that may be accessed by the applications 716 and 718 may be limited. In some examples, a patient of the medical provider network may use one of the applications 716, 718 to access his or her own medical-related data. In this example, the identity of the patient may be verified in accordance with techniques described herein.

The user devices 706-714 are any suitable user devices capable of running the applications 716-724. The user devices 706-714 are examples of the user device 228. In some examples, the user devices include: mobile phones, tablet computers, laptop computers, wearable mobile devices, desktop computers, set-top boxes, pagers, and other similar user devices. In some examples, at least some of the user devices 706-714 are the same devices as at least some of the one or more components 410-418. In some examples, the user devices 706-714 may include complementary layers to the application/device layer 320 and/or the receiving layer 302. For example, the user devices 706-714 may include a transmission layer, a generation layer, and/or a receiving layer to communicate data at the application/device layer 320 and at the receiving layer 302.

Figure 8:
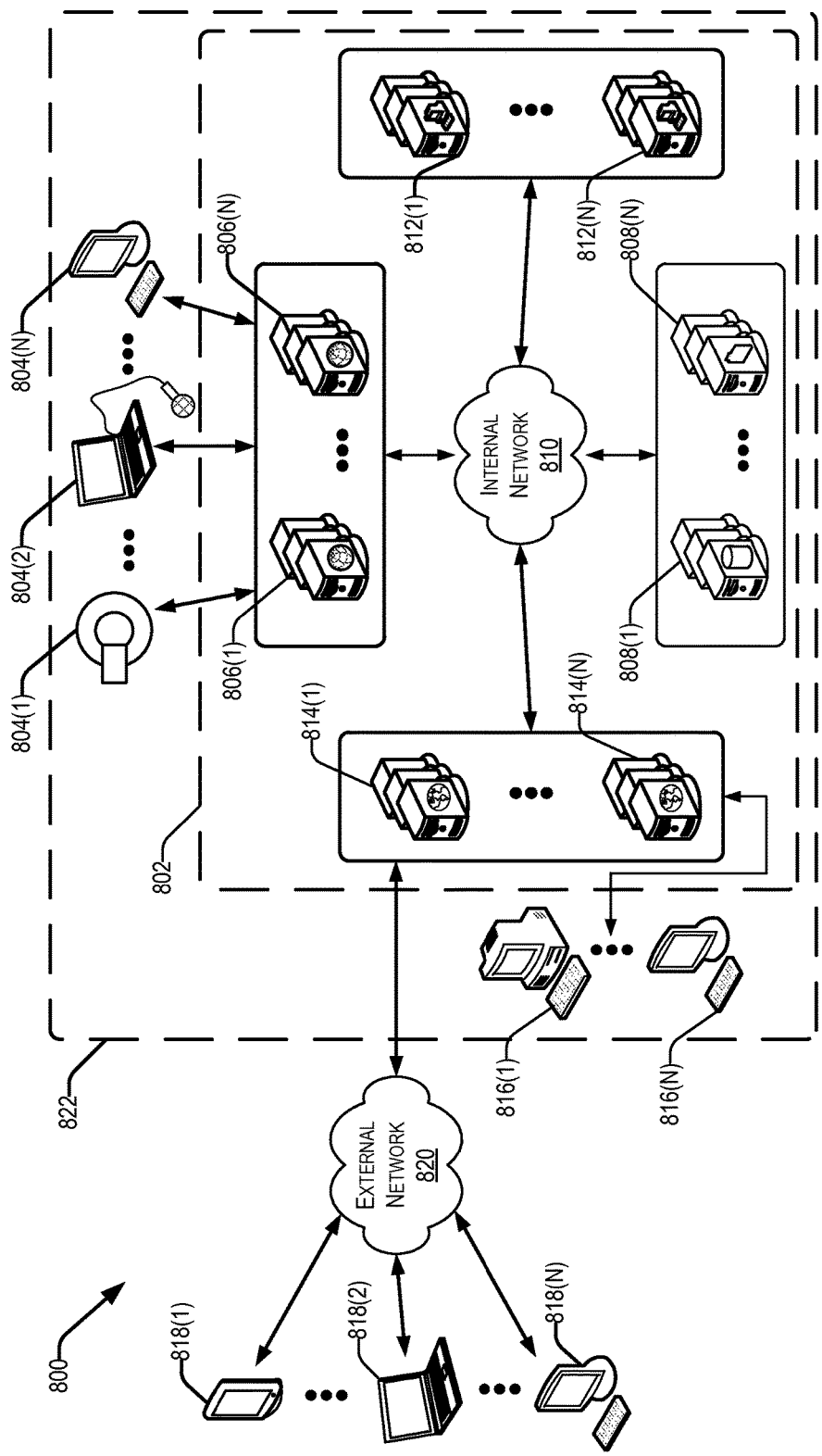
FIG. 8 illustrates a block diagram of an example of a medical provider network, in accordance with certain embodiments of the present disclosure.

Turning now to FIG. 8, a medical provider network 800 is shown in accordance with an embodiment of the invention. The medical provider network 800 includes an internal organization 822 including a transformative integration engine 802. The transformative integration engine 802 is an example of the transformative integration engine 202 previously discussed. The medical provider network 800 is illustrated as an example configuration for implementing the techniques described herein. In particular, a configuration of elements as illustrated in FIG. 8, at least in some examples, communicates according to the layers of the medical architecture stack 300. For example, the internal organization 822 includes generation components 804(1), 804(2), and 804(N) which provide medical-related data to aggregation servers 806(1)-806(N).

The generation components 804(1), 804(2), and 804(N) operate in accordance with the receiving layer 302. In some examples, the generation component 804(1) is an MRI machine, a type of medical equipment, the generation component 804(2) is computer with a data collection device, a type of lab system, and the generation component 804(N) is a terminal, which is a type of business component or clinical component. The aggregation servers 806(1)-806(N) operate in accordance with the aggregation layer 304. The aggregation servers 806(1)-806(N) share medical-related data with data storage servers 808(1)-808(N) via one or more internal network(s) 810. In some examples, the internal network 810 is any suitable network capable of handling transmission of medical-related data. For example, the internal network 810 may be any suitable combination of wired or wireless networks. In some examples, the internal network 810 may include one or more secure networks. The data storage servers 808(1)-808(N) are configured to store medical-related data in accordance with the active unified data layer 308. The data storage servers 808(1)-808(N) include database servers, file storage servers, and other similar data storage servers.

Access management servers 812(1)-812(N) manage access to the medical-related data retained in the data storage servers 808(1)-808(N). The access management servers 812(1)-812(N) communicate with the other elements of the medical provider network 800 via the internal network 810 and in accordance with the access management layer 310.

Interface servers 814(1)-814(N) provide one or more interfaces applications to interact with the other elements of the medical provider network 800. The interface servers 814(1)-814(N) provide the one or more interfaces and communicate with the other elements of the medical provider network 800 via the internal network 810 and in accordance with the interface layer 316. The interfaces generated by the interface servers 814(1)-814(N) can be used by internal user devices 816(1)-816(N) and external user devices 818(1), 818(2), and 818(N) to interact with elements of the medical provider network 800.

The internal user devices 816(1)-816(N) are examples of the user devices 706-714. In some examples, the internal user devices 816(1)-816(N) run applications for patients, doctors, specialists, nurses, administrative professionals, network administrators, business leaders, and others that access the other elements of the medical provider network 800 via the interfaces generated by the interface servers 814(1)-814(N). As an additional example, the external user devices 818(1), 818(2), and 818(N) run applications developed by third parties for patients, doctors, specialists, nurses, administrative professionals, network administrators, business leaders, and others that access the other elements of the medical provider network 800 via the interfaces generated by the interface servers 814(1)-814(N).

The external user devices 818(1), 818(2), and 818(N) access the interfaces via external network 820. In some examples, the external network 820 is an unsecured network such as the Internet. The external user devices 818(1), 818(2), and 818(N) are examples of the user devices 706-714. The external user device 818(1) is a mobile device. In some examples, the mobile device may be configured to run an application to access the medical provider network 800. Similarly, the other external user devices 818(2)-818(N) run applications that enable them to access the medical provider network 800. While the medical provider network 800 is shown as implemented using discrete servers, it is understood that it may be implemented using virtual computing resources and/or in a web-based environment.

A variety of geolocation techniques can be used to locate a device or vehicle. For example, a device can receive signals from a plurality of sources, such as global positioning system (GPS) satellites, cell phone towers or WiFi access spots. Data from the signals (e.g., identifying a source location and/or being indicative of a signal latency) can then be used to estimate a location of the device. Navigation systems can use such location estimations and identified destination locations to present information such as a route to arrive at a destination and/or an expected arrival time. While the information can be extremely useful to a user near the device, other parties may also have high interest in the data.

Embodiments of the invention track location data of dispatch vehicles and modify metrics for resource-allocation systems based on the data. For example, an institution can identify whether a dispatch vehicle has arrived at a destination location by a target time and/or an extent to which an actual or estimated arrival time differed from the target time. The institution can identify a resource-allocation system associated with the dispatch vehicle and adjust a metric of the resource-allocation system based on the data. The metrics can subsequently be used to influence assignments of tasks to various transportation entities. For example, tasks can be preferentially presented to or assigned to resource-allocation entities with high metrics.

In some embodiments, a task scheduling system generates and/or accesses a task to be assigned to a resource-allocation system. A task can include, for example, transporting a load from a first location to a destination, modifying an electronic record so as to reflect a current or predicted presence (or lack thereof) of a load in a given system, preparing a load for transport and/or releasing a load from a system. Each task can be associated with a performance time, which can include, for example, an absolute time (e.g., date and time) or time period at or during which (for example) it is desired that part or all of the task is to be completed. For example, it can be desired that a resource can access to a load at a time within a target time period.

The task scheduling system can generate a first signal that indicates that the system is accepting offers to perform the task. The first signal can include the target time. The first signal can be sent to each of one or more resource-allocation systems, which are configured to control resources capable of performing tasks. The task scheduling system can receive a second signal from each of a subset (e.g., an incomplete or complete subset) of the set that includes an offer to accept an assignment of the task. Thus, the second signal can correspond to an indication that a resource managed by the associated resource-allocation system is available to perform the task in compliance with the target time. The task scheduling system can then select a resource-allocation system to assign the task to and transmit a third signal to the selected system that is indicative of the assignment.

The task scheduling system can select between resource-allocation systems with regard to identifying systems to receive the first signal and/or to identifying a system to be assigned the task. This selection can be biased based on a metric of each of one or more systems. The metric can be based on performance characteristics of previously assigned tasks, such as whether a particular portion (or all) of a task was completed by a target time or within a target time (e.g., time window). The same or a different metric can also relate to, for example, a current or previous delay or reliability of responding to indications of acceptances of offers for tasks or assignments of a task.

In some instances, the task scheduling system further identifies a type of task-performing resource suited to handle a particular task by, e.g., identifying a characteristic of a load involved in the task and mapping the load characteristic to a resource type. For example, an identifier of a load to be involved in a task can be used to retrieve an electronic record that associates the load identifier along with an indication as to whether any particular capabilities are required for appropriate performance of the task. The selection (regarding which system(s) are to receive the first signal and/or which system is assigned the task) can further be based on data indicating which systems manage at least one resource of the identified type.

Once a task has been assigned to a resource-allocating system, the task scheduling system can maintain communication with the resource-allocating system so as to monitor data pertinent to actual or expected progress of completion of the task. This progress can reflect how timely particular resources were positioned and/or prepared to accept loads of assigned tasks.

Figure 9:
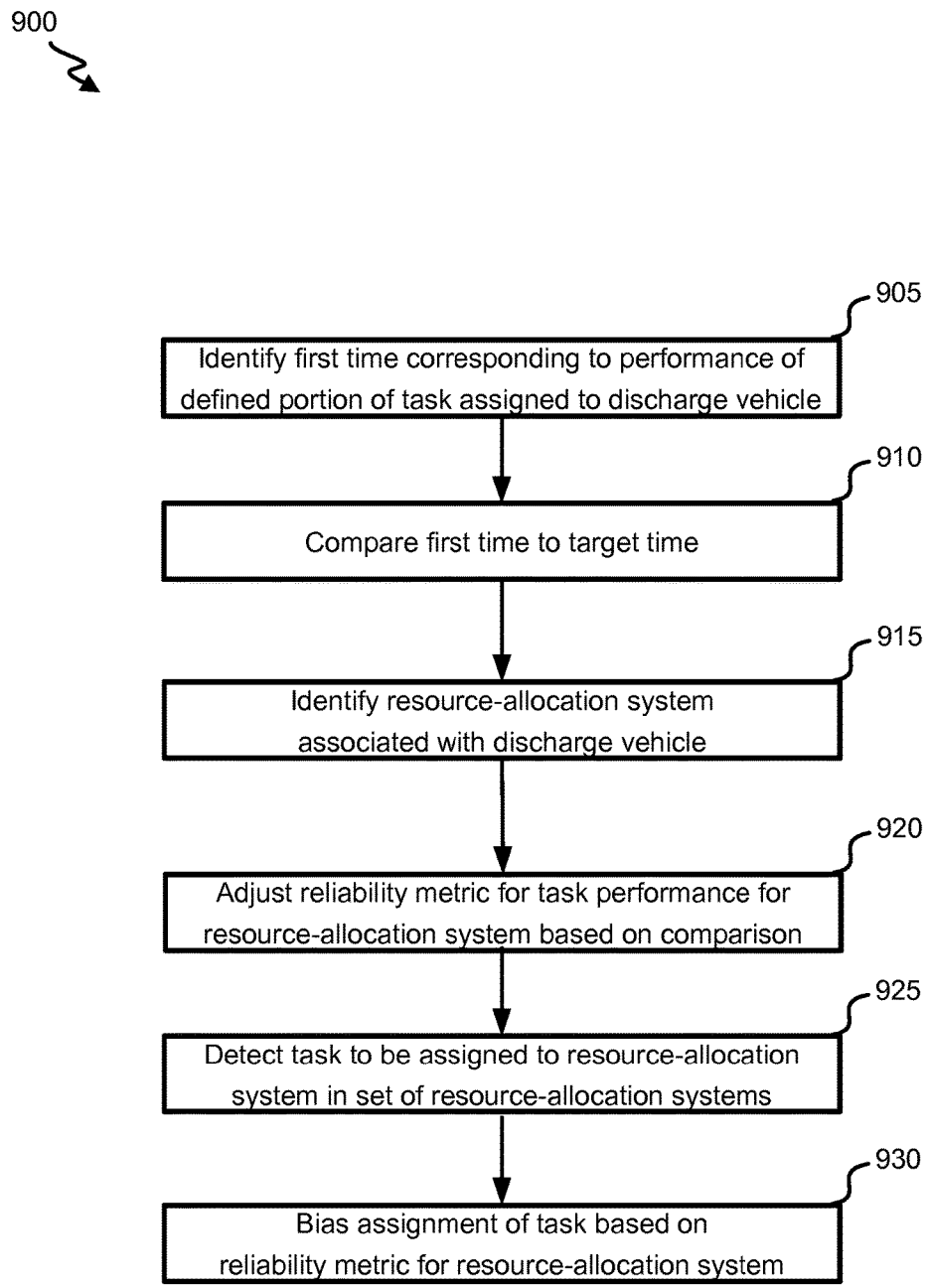
FIG. 9 illustrates a flowchart of an embodiment of a process for using location data of discharge vehicles for management of distributions of task assignments, in accordance with certain embodiments of the present disclosure.

FIG. 9 illustrates a flowchart of an embodiment of a process 900 for using location data of discharge vehicles for management of distributions of task assignments. Process 900 can be performed in part or in its entirety by a task scheduling system.

Process 900 begins at block 905 where a first time is identified that corresponds to a performance of a defined portion of a task assigned to a discharge vehicle. The first time can include an actual or estimated time at which the defined portion is completed. In some instances, block 905 includes determining whether the defined portion is completed by a particular time and, if not, identifying when the portion is completed (e.g., so as not to detect early completion). In some instances, early performances are also identified.

For example, the first time can identify a time at which the discharge vehicle (e.g., or other resource) is prepared to accept and/or has accepted a load of the task. In some instances, the first time relates to a time at which the discharge vehicle (e.g., or other resource) is located at a particular location corresponding to the task. Thus, the first time can be identified based on location tracking of the resource. Accordingly, a signal can be received from the vehicle or an intermediate system (e.g., an associated resource-allocation system or a system receiving input indicating that the portion has been completed) that identifies a location of the discharge vehicle (e.g., geographic coordinates and/or whether it is at a particular location). When the location matches a location corresponding to the portion of the task, a first time can be defined as a time at which the signal was received and/or a time included in the signal.

At block 910, the first time is compared to a target time. The target time can include a particular time point (e.g., date and time of day) or a time window (e.g., date and range of times or a time threshold). The target time can include one associated with the task and/or the portion of the task. For example, the target time can include a time by which or during which the discharge vehicle is to be prepared to accept a load and/or is to be located at a particular location (e.g., as specified in the task).

In some instances, a target time for completing the defined portion of the task is identified. The target time can include a time at which the defined portion was scheduled to be completed. The target time can be identified by retrieving data corresponding to a particular task, discharge vehicle and/or resource-allocation system. For example, a received signal can be received that identifies an assigned task and is also indicative of the first time. An identifier of the task can be looked up in a scheduling data structure so as to identify one or more target times for the task.

At block 910, the first time is compared to the target time. The comparison can include, for example, determining whether the first time preceded the target time and/or an extent to which the first time differed from the target time (e.g., a delay in completion of the defined portion). In some instances, the comparison can account for potentially intervening factors, such as traffic conditions near a location corresponding to the defined portion of the task.

At block 915, a resource-allocation system associated with the discharge vehicle is identified. The resource-allocation system can include one to which the task was assigned by a task scheduling system. The resource-allocation system can manage and/or coordinate a schedule for each of one or more resources (e.g., the discharge vehicle). For example, the resource-allocation system can receive task assignments from each of one or more task scheduling systems and can assign corresponding tasks to appropriate resources. As one particular illustration, the resource-allocation system can coordinate a schedule of one or more discharge vehicles.

The resource-allocation system can be identified within a received signal (e.g., identifying the first time) and/or can be determined using other information (e.g., an identifier of the task and/or an identifier of the discharge vehicle). For example, a signal can identify a particular discharge vehicle and a first time at which the discharge vehicle arrived at a first location as specified in a task. A scheduling system can then look up an identifier of the discharge vehicle in a data structure that associates particular vehicles with particular resource-allocation systems. As another example, a signal can identify that a particular discharge vehicle arrived at a first time to pick up a particular patient. A scheduling system can then look up an identifier of the patient in a data structure that associates patient identifiers with task identifiers and identifiers of resource-allocation systems assigned to handle the tasks.

At block 920, a reliability metric for task performance for the resource-allocation system is adjusted based on the comparison. The reliability metric can reflect or relate to, for example, a probability that particular portions of tasks assigned to the resource-allocation system are completed prior to a target time and/or a statistic reflecting delays in completing the defined portion. For example, for tasks that indicate that patients are to be picked up at particular locations in a discharge vehicle (e.g., ambulance, wheelchair vehicle or helicopter) and transported to destination locations, the metric can include a percentage of time that the vehicle was at a pick-up location prior to or at a target pick-up time or an average or median difference between a target pick-up time and actual pick-up times. Metrics can generally apply to resource-allocation system or can be specific based on factors such as resource types, particular discharge vehicles, particular drivers, particular pick-up locations, types of task portions, etc.

Adjusting the metric can include, for example, updating a probability or statistic. In some instances, the updating can occur in a manner that reduces relative influence on older data.

At block 925, a task to be assigned to a resource-allocation system is detected. The task can include one that requires a discharge vehicle, such as transporting a load (e.g., patient or piece of equipment) from a first location to a destination location. In some instances, data can indicate that task-assignment relationships have been established between a task scheduling system and each of a set of resource-allocation systems. The set of resource-allocation systems can include the resource-allocation system for which the reliability metric was adjusted at block 920.

At block 930, an assignment of the task can be biased based on the reliability metric that was adjusted at block 920. Effecting assignment biases can include, for example, transmitting signals identifying a potential task assignment to an incomplete subset of the set of resource-allocation systems (e.g., those with favorable metrics), transmitting a signal identifying a potential task assignment to one resource-allocation system (e.g., with a favorable metric) before a similar signal is transmitted to another system, identifying fewer constraints for a task in a signal transmitted to one resource-allocation system as compared to a corresponding task as identified to another system and/or biasing actual task assignments towards systems with favorable metrics (e.g., when multiple resource-allocation systems transmit signals corresponding to an offer to accept an assignment of the task). The bias can occur by implementing a ranking, order or weighting. The bias can occur to favor, for example, resource-allocation systems associated with reliability metrics indicating that tasks previously assigned to the systems (or defined portions thereof) where consistently and/or timely performed.

Figure 10:
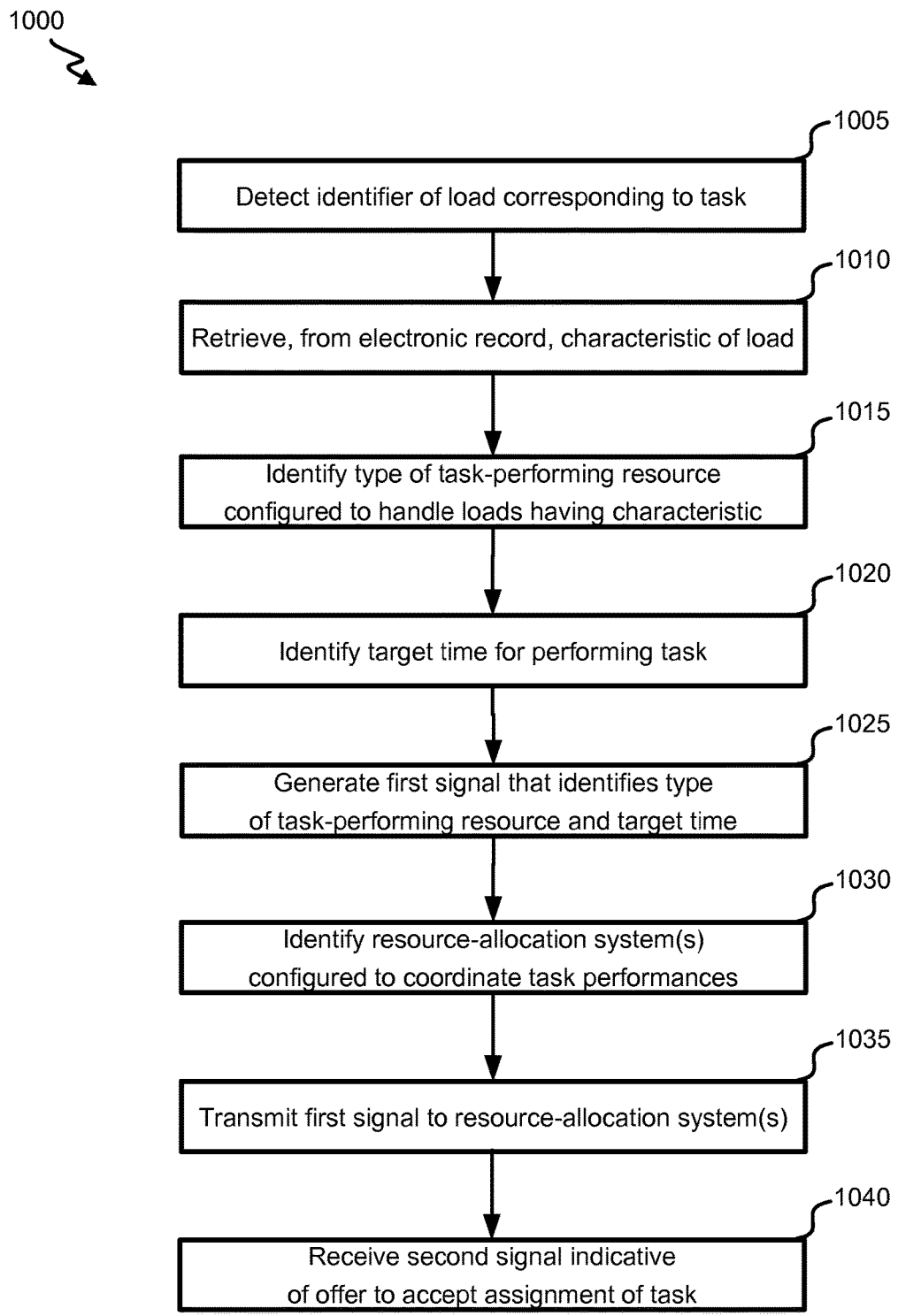
FIG. 10 illustrates a flowchart of an embodiment of a process for collecting task specifications and identifying appropriate task-performing resources, in accordance with certain embodiments of the present disclosure.

FIG. 10 illustrates a flowchart of an embodiment of a process 1000 for collecting task specifications and identifying appropriate task-performing resources. Process 1000 begins at block 1005 where an identifier of a load of a task is detected. The detection can include, for example, detecting a scan of an electronic device or electronic tag corresponding to the load or detecting input that identifies the load. The load can be one that is to be transported from a first location to a second location by a resource, such as a discharge vehicle. The load can include a piece of equipment, medication, lab samples or a patient.

The identifier can be used to access an electronic record corresponding to the load. At block 1010, a characteristic of the load can be retrieved from the record. The characteristic can include a physical characteristic (e.g., a weight or dimension) or a handling requirement (e.g., appropriate temperature and/or required nearby medical equipment or personnel). In one instance, the characteristic identifies a degree to which a patient is medically stable (or instable) and/or requiring intense care during transport.

At block 1015, a type of task-performing resource configured to handle or accept loads having the characteristic is identified. For example, block 1015 can include identifying a threshold speed, size or dimension of a resource. As another example, block 1015 can include identifying a functionality, capability or component of a resource (e.g., that it must include a transcutaneous cardiac pacemaker or a particular medication or that a paramedic be physically available in or near the resource to control task performance). As yet another example, block 1015 can include identifying whether a task-performing resource must be an advanced life support ambulance.

At block 1020, a target time for performing at least part of the task is identified. For example, the target time can include a time at which it is desired that the assigned that the assigned task is initiated, that a resource is available to begin performing the assigned task, that a resource is located at a particular (e.g., pick-up or destination) location corresponding to the task, that the resource has begun handling the load, that the resource is at a destination location, that a defined portion of the task has been completed or that the task has been entirely completed.

The target time can be identified, for example, based on scheduling objectives of an institution, task parameters (e.g., how far a load must be transported) and/or the characteristic. The target time can include an absolute time (e.g., November 20 at 9 am) or a time range (e.g., November 20, 9-9:15 am).

At block 1025, a first signal is generated that identifies the type of task-performing resource and the target time. The first signal can correspond to an indication that a task corresponding to data in the first signal is requiring assignment or will be assigned. The first signal can correspond to an indication that a task scheduling system is accepting indications from resource-allocation systems that such resource-allocations are available and/or equipped to handle the task. In some instances, the first signal includes additional information about the task, such as one or more geographical locations involved in the task (e.g., a pick-up and/or destination location), an identification of an associated task scheduling system or institution and/or a deadline for responding to the first signal.

At block 1030, one or more resource-allocation systems to receive the first signal are identified. In some instances, each of a set of resource-allocation systems is configured to control, schedule and/or coordinate use of one or more resources. An institution corresponding to a task scheduling system can have an established working relationship with an entity associated with each of the set of resource-allocation systems that supports a coordinated approach for scheduling resources to meet priorities of the task scheduling system. In some instances, the task scheduling system maintains and/or has access to a data store that indicates, for each of the set of resource-allocation systems, identifying information (e.g., a name of a corresponding entity), communication-protocol information (e.g., a mode of communication or contact identifier), an identification of each type of resource coordinated by the resource-allocation system, a quantity of available resources (e.g., generally or of a given type), a resource constraint (e.g., geographic limits as to where a resource can be used) and/or a performance metric.

In some instances, the one or more resource-allocation systems includes all of the resource-allocation systems in the set. In some instances, an incomplete subset is selected. For example, the incomplete subset can include systems associated with performance metrics above an absolute or relative threshold (e.g., within the top five in a set) and/or with at least a threshold number (e.g., 1 or within the top three amongst the set) of resources of a type matching that identified at block 1015.

At block 1035, the first signal is transmitted to the identified resource-allocation systems. The first signal can be transmitted, for example, wirelessly and over a network (e.g., the Internet or a phone network). In some instances, blocks 1030 and 1035 can be repeatedly performed. For example, the first signal can be initially sent to a first resource-allocation system. If the first resource-allocation system does not respond to the first signal within a prescribed time period and/or declines the task, the a second resource-allocation system can be identified.

At block 1040, a second signal is received from a resource-allocation system that is indicative of an offer to accept assignment of the task. The second signal can indicate that a resource associated with the resource-allocation system is available, can identify an identifier or specification of the available resource, and/or can identify one or more times (e.g., start times, end times and/or time periods) that the resource is available. For example, a first signal can indicate that a task would involve a morning pick-up of a patient at a particular hospital in an ambulance, and a second signal can indicate that a resource-allocation system could schedule an advanced life support ambulance to arrive at the hospital any time before 10 am or a basic life support ambulance to arrive at the hospital before 9 am.

In some instances, the second signal includes an offer that, at least in part, does not match the task. For example, a first signal may indicate that a task would involve a morning pick-up in a wheelchair vehicle. A resource-allocation system may detect that such a resource is not available during the requested time but may respond with an offer for pick-up at 1 pm.

Thus, process 1000 can involve automatically identifying resource specifications appropriate for a particular task. Such specifications can be used to communicate the task to select resource-allocation systems likely to include resources with the identified specifications and/or to identify to resource-allocation systems as to what types of resources would be required for task performance. Efficiency of scheduling tasks and performance of tasks can thereby be improved.

Figure 11:
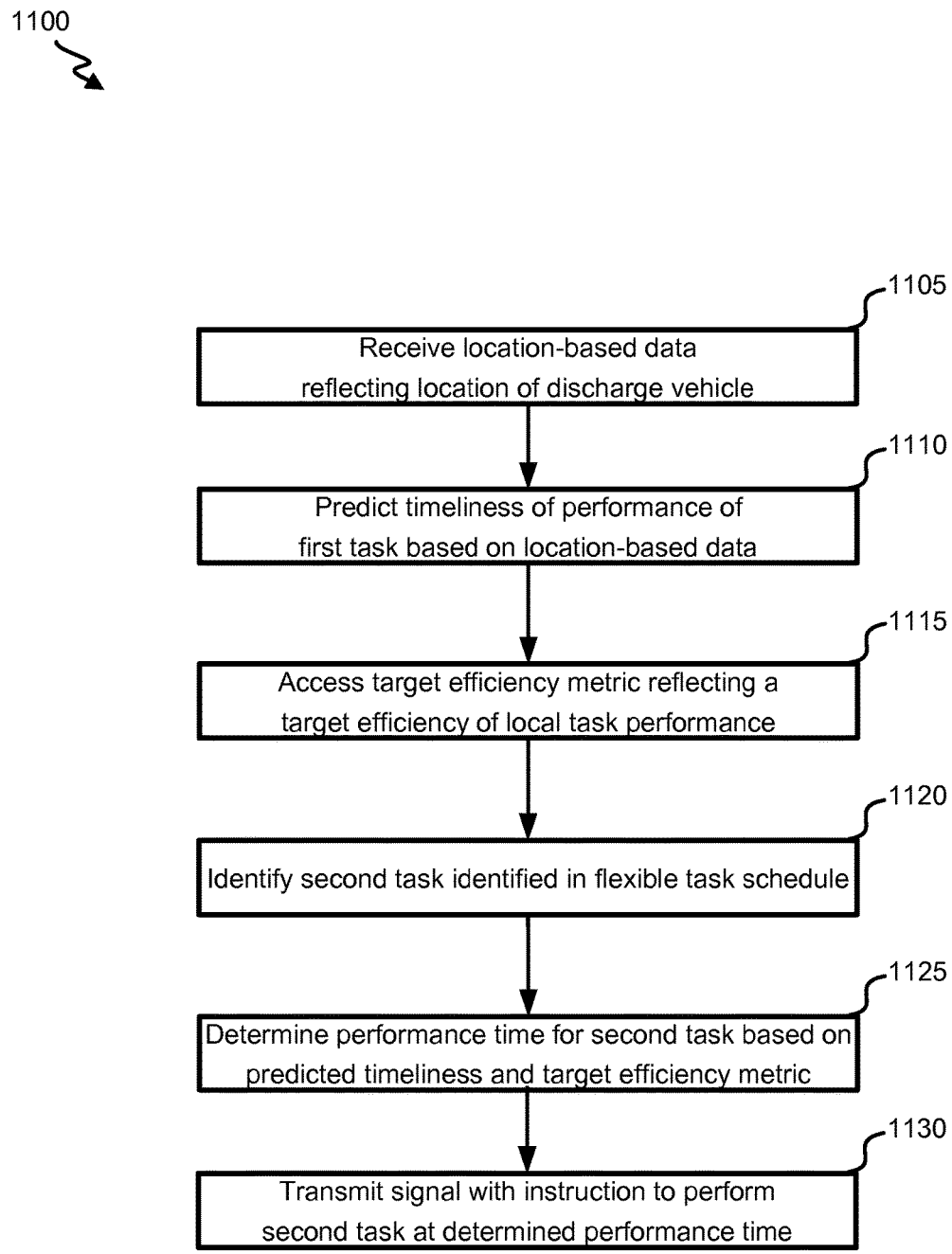
FIG. 11 illustrates a flowchart of an embodiment of a process for using location data of discharge vehicles for electronically adjusting scheduled tasks, in accordance with certain embodiments of the present disclosure.

FIG. 11 illustrates a flowchart of an embodiment of a process 1100 for using location data of discharge vehicles for electronically adjusting scheduled tasks. Process 1100 begins at block 1105 where location-based data reflecting a location of a discharge vehicle is received. The location-based data can be received from a resource-allocation system. The resource-allocation system can include a distributed system that includes a location-tracking component in the discharge vehicle, or it can otherwise be in communication with a location-tracking system in the discharge vehicle.

The location-based data can identify, for example, a location of the discharge vehicle (e.g., a stop or geographic coordinates) or a distance that the discharge vehicle is from a location (e.g., from a pick-up location corresponding to a task). In some instances, the location-based data includes a time, such as an estimated arrival time (e.g., 20 minutes or at 3:10), that is based on a location of the discharge vehicle. Location-based data can be based on signals (e.g., from GPS satellites or other sources) received by a receiver in a component of or device in the discharge vehicle.

At block 1110, a timeliness of performance of a first task is predicted based on the location-based data. The prediction can include, for example, predicting whether all or a defined portion (e.g., a pick-up or an arrival of a discharge vehicle) of a task will be completed by a target time and/or predicting an extent to which completion of a defined portion or all of the task will be delayed beyond a target time. In some instances, the prediction can include predicting whether a defined portion (or all) of the task will be performed by a target time plus a defined buffer time.

At block 1115, a target efficiency metric that reflects a target efficiency of local task performance is accessed. The target efficiency metric can relate to, for example, a number of local tasks (e.g., discharges) to be performed during a defined time period, spacing of tasks (e.g., discharges) across a defined time period or delays between related tasks (e.g., preparing a patient for discharge and discharging the patient). For example, a target efficiency metric can indicate that, amongst a set of patients to be discharged during a day, it is desired that 50% of those patients be discharged before 1 pm.

The target efficiency metric can be identified based on stored data, input (e.g., received from an institution agent) and/or a learning technique that identifies metrics associated with positive results (e.g., positive health outcomes, such as low mortality and low readmission; high efficiency, such as attending to a large number of patients per day; low waiting times; etc.).

At block 1120, a second task is identified. The second task can include one that is flexibly scheduled, in that a time at which part or all of the task is to be performed can be adjusted. Whether a task is flexibly scheduled can depend on, for example, whether performance of the task has begun or a priority of the task (e.g., where tasks involving urgent health matters may be identified as inflexible).

In some instances, the second task can include one that is related to the first task. For example, the first task can include transporting a first patient from a hospital to a destination, and a second task can include discharging the first patient from the hospital or preparing the first patient from discharge. Thus, if the first task is delayed, it may be desirable to reschedule the related second task so as to avoid or reduce a waiting period between the tasks.

In some instances, the second task can include on that is or is related to a task that is of a similar type as the first task. For example, the first task can include transporting a first patient from a hospital to a destination, and a second task can include discharging a second patient from the hospital. Thus, if the first task is delayed, rescheduling the second task can aid an institution in nonetheless reaching a target metric (e.g., number of discharges per time period).

At block 1125, a performance time (e.g., a target time) for the second task is determined based on the predicted timeliness and/or target efficiency metric. For example, at block 1110, it can be predicted that the first task will be completed 30 minutes late. A performance time of a related second task can then be adjusted to be 30 minutes later than initially scheduled. As another example, at block 1110, it can be predicted that a portion of the first task that was initially scheduled to be completed during a first time period will be completed in a second period. The performance time for a portion of the second task can then be set to be (or to be within) the first time period.

At block 1130, a signal is transmitted with an instruction to perform the second task (or portion thereof) at the determined performance time. The signal can be transmitted to, for example, a device of a care provider, a resource-allocation system or other device or system that facilitates performance of a task. In some instances, the signal can include an option to confirm, accept and/or reject the instruction.

Thus, by monitoring location-based data of discharge vehicles, a schedule involving multiple tasks, resources and/or entities can be dynamically reconfigured to promote achievement of target metrics even when faced with delays.

Figure 12:
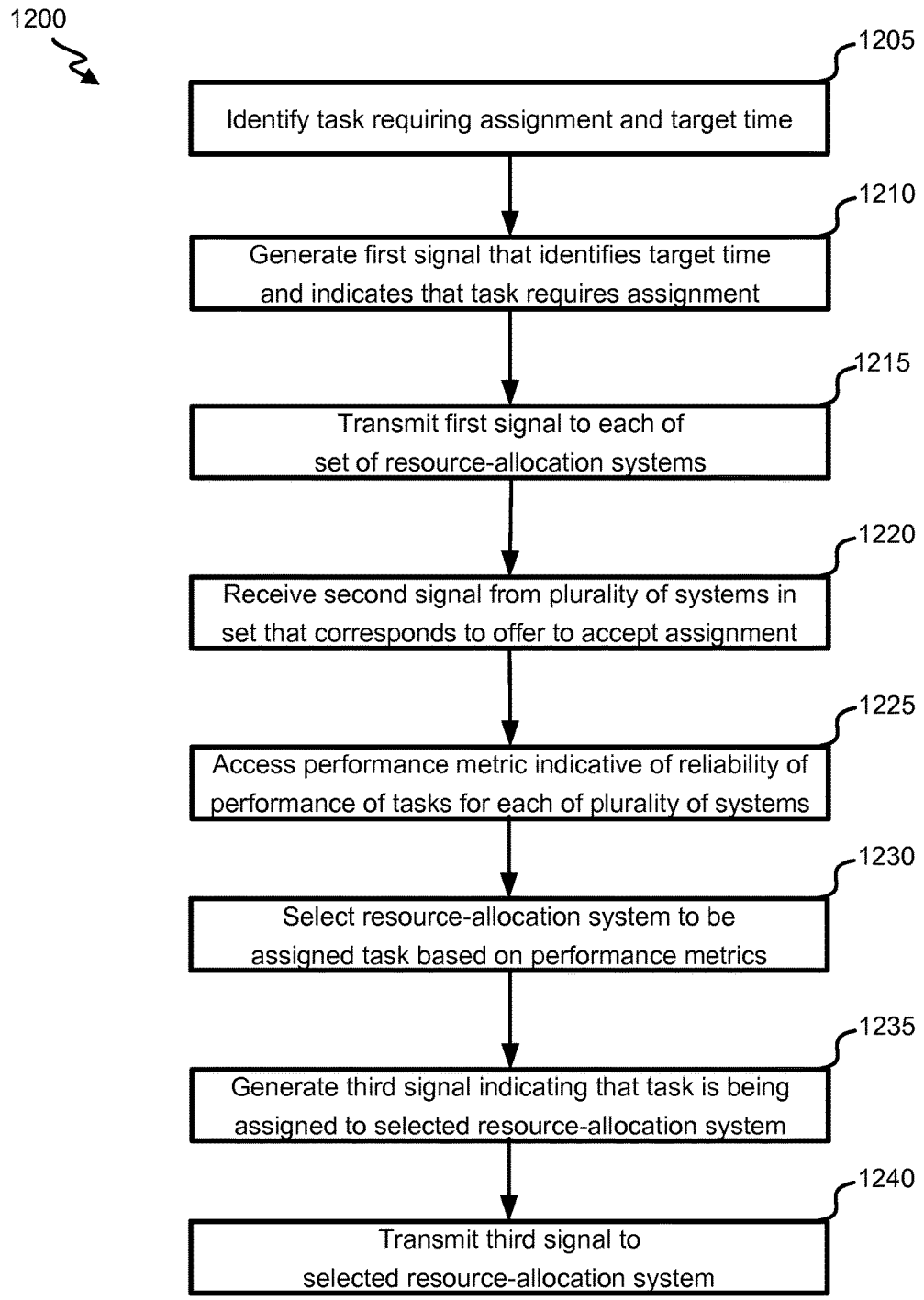
FIG. 12 illustrates a flowchart of an embodiment of a process for assigning tasks based on empirical performance assessments of resource-allocation systems, in accordance with certain embodiments of the present disclosure.

FIG. 12 illustrates a flowchart of an embodiment of a process 1200 for assigning tasks based on empirical performance assessments of resource-allocation systems. Process 1200 begins at block 1205 where a task requiring assignment to a resource-allocation system is identified. Assignment of the task can result in the assigned resource-allocation system configuring a resource associated with the resource-allocation system to perform the task. The task can include, for example, transporting a load between locations, such as transporting a patient from a medical institution to a destination location.

A target time for the task can also be identified at block 1205. The target time can be based on a target metric, a characteristic of a load involved in the task (e.g., medical stability of a patient), a queue of other tasks requiring a resource (e.g., also required by the task or that will be freed upon performance of the task), etc. In some instances, the target time is identified via user input. The target time can include a time at which a defined portion or all of the task is to be completed. Thus, in some instances, multiple target times can be identified for a given task.

At block 1210, a first signal corresponding to the task is generated that identifies the target time and is indicative that the task is requiring assignment. At block 1215, the first signal is transmitted to each resource-allocation system of a set of resource-allocation systems;

In some instances, each of the set of resource-allocation systems is configured to control, schedule and/or coordinate use of one or more resources. An institution corresponding to a task scheduling system can have an established working relationship with an entity associated with each of the set of resource-allocation systems that supports a coordinated approach for scheduling resources to meet priorities of the task scheduling system.

In some instances, the task scheduling system maintains and/or has access to a data store that indicates, for each of a group of resource-allocation systems, identifying information (e.g., a name of a corresponding entity), communication-protocol information (e.g., a mode of communication or contact identifier), an identification of each type of resource coordinated by the resource-allocation system, a quantity of available resources (e.g., generally or of a given type), a resource constraint (e.g., geographic limits as to where a resource can be used or time limits as to when a resource can be used) and/or a performance metric. The set of resource-allocation systems can include all of the group of resource-allocation systems or an incomplete subset thereof. The incomplete subset can be identified based on, for example, types of resources associated with the systems (e.g., to selectively include systems associated with types of resources appropriate for the tasks), performance metrics (e.g., to selectively include systems associated with above-threshold metrics) and/or constraints.

At block 1220, a second signal can be received from each of a plurality of resource-allocation systems in the set of resource-allocation systems. Each second signal can correspond to an offer to accept an assignment of the task. The second signal can indicate that a resource associated with the resource-allocation system is available, can include an identifier or specification of the available resource, and/or can identify one or more times (e.g., start times, end times and/or time periods) that the resource is available.

At block 1225, a performance metric is accessed for each resource-allocation system of the plurality of resource-allocation systems. The performance metric can be indicative of a reliability of performance of tasks previously assigned to the resource-allocation system. The performance metric can reflect and/or be based on a percentage of tasks previously assigned to the system that were completed (or with a defined portion being completed) by a target time and/or a difference between performance times and target times. For example, a performance metric can include an index reflecting a weighted average (e.g., highly weighting recent data) of a delay between a target pick-up time and an actual pick-up time. In some instances, a set of performance metrics can be associated with a single resource-allocation system. The performance metrics can be analyzed collectively or one or more select performance metrics (e.g., applying to the identified task) can be accessed.

At block 1230, a resource-allocation system is selected from amongst the plurality of resource-allocation systems to be assigned the task. The selection can be based on the accessed performance metrics. For example, the selection can be biased towards systems associated with high metrics. To illustrate, a resource-allocation system associated with a highest performance metric amongst those accessed can be selected or a first resource-allocation system to have responded to the first signal and to be associated with a performance metric above a threshold can be selected.

At block 1235, a third signal is generated that indicates that the task is being assigned to the selected resource-allocation system. In some instances, the third signal includes additional information about the task that was not present in the first signal. For example, the third signal can include a name of a patient and/or a more particular location. The third signal can further include an identifier for the task and/or instructions to report statuses of the task performance. At block 1240, the third signal is transmitted to the selected resource-allocation system.

Thus, process 1200 illustrates a technique for using performance metrics to adjust assignments of tasks. Resource-allocation systems associated with performance metrics indicative of consistent high-quality performance can be preferentially notified of potential task assignments and/or assigned tasks.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A system for controlling resource allocation and task processing, the system comprising:
   a transformative integration engine communicatively coupled with a transaction management engine, the transformative integration engine comprising:
      one or more aggregation servers communicatively coupled to one or more detecting components and configured to aggregate data from the one or more detecting components;
      one or more data storage servers communicatively coupled to the one or more aggregation servers and configured to store the data aggregated in a unified data layer of the system; and
      one or more interface servers that are communicatively coupled to one or more networks and to one or more interfaces that receive a first set of electronic communications from one or more detection devices that detect load identifiers;
   the transaction management engine to track transmissions of electronic communications communicated via the one or more interfaces, the tracking transmissions comprising detecting an electronic communication of the first set of electronic communications, the electronic communications comprising an electronic identifier of a load, wherein the load identifiers comprises the electronic identifier of the load;
   the transformative integration engine to:
      consequent to detecting the electronic identifier, retrieve, via at least one data storage server of the one or more data storage servers and based at least in part on the electronic identifier, a characteristic of the load from an electronic record stored in the unified data layer;
      identify i) a first task specification for a first task associated with the load, ii) a target time for performing the first task, and iii) a type of task-performing resource configured to accept loads having the characteristic;
      access a respective metric for each resource-allocation system in a plurality of resource-allocation systems that is indicative of a respective reliability of performance of tasks previously assigned to the resource-allocation system;
      bias, based at least in part on the metrics accessed, an assignment of the first task with respect to a subset of the plurality of resource-allocation systems, and, consequent to the biasing, assigning the first task to a particular resource-allocation system from the subset;
      generate a first signal corresponding to the first task that identifies the target time and is indicative of the assignment of the first task;
      transmit the first signal to the particular resource-allocation system;
   the transaction management engine further to detect one or more subsequent electronic communications comprising location-based data that is communicated from at least one of the one or more detecting components and based at least in part on one or more sensors detecting indicators of one or more locations of the task-performing resource;
   the transformative integration engine further to:
      predict a timeliness of performance of the first task based at least partially on the location-based data;
      access a target efficiency metric reflecting a target efficiency of task performance;
      access a flexible task schedule to identify a second task identified;
      determine a performance time for the second task to be performed based at least partially on the predicted timeliness of performance of the first task and the target efficiency metric; and
      transmit a second signal with an instruction to perform the second task at the performance time determined;
   the transaction management engine further to:
      track subsequent transmissions so that electronic communications with data corresponding to the first task and/or the second task are detected; and
   the transformative integration engine further to generate one or more alerts based at least in part on receiving tracked data.

2. The system for controlling resource allocation and task processing as recited in claim 1, wherein the one or more interfaces receive a second set of electronic communications from the one or more detecting components that are communicatively coupled to the one or more sensors, the location-based data comprising geolocation data.

3. The system for controlling resource allocation and task processing as recited in claim 2, the transformative integration engine further to identify the target efficiency metric based at least in part on previously stored data in the unified data layer and applying a learning technique that identifies metrics associated with positive results.

4. The system for controlling resource allocation and task processing as recited in claim 3, the transaction management engine further to receive the electronic communication of the first set of electronic communications from at least one detecting component of the one or more detecting components, wherein the at least one detecting component detects a scan of an electronic device or an electronic tag corresponding to the load.

5. The system for controlling resource allocation and task processing as recited in claim 4, the tracking subsequent transmissions comprising:
identifying a first time corresponding to performance of a defined portion of the first task;
comparing the first time to a target time; and
adjusting the respective metric for the particular resource-allocation system based at least partially on the comparison of the first time to the target time, wherein the respective metric comprises a metric for task performance.

6. The system for controlling resource allocation and task processing as recited in claim 5, wherein the biasing the assignment of the first task comprises selecting the subset of the plurality of resource-allocation systems, the selection being at least partially based on the metrics accessed, and selectively transmitting one or more allocation requests to each resource-allocation system in the subset.

7. The system for controlling resource allocation and task processing as recited in claim 6, wherein the selectively transmitting the allocation requests to each resource-allocation system in the subset comprises sequentially transmitting each allocation requests of a plurality of allocation requests to one or more of the resource-allocation systems of the plurality of resource-allocation systems according to a ranked order.

8. A method for controlling resource allocation and task processing, the method comprising:
aggregating, by a transformative integration engine communicatively coupled with a transaction management engine, data from one or more detecting components, the transformative integration engine comprising one or more aggregation servers communicatively coupled to the one or more detecting components;
storing, by one or more data storage servers of the transformative integration engine, the data aggregated in a unified data layer;
receiving, via one or more interfaces, a first set of electronic communications from one or more detection devices that detect load identifiers;
tracking, by the transaction management engine, transmissions of electronic communications communicated via the one or more interfaces, the tracking transmissions comprising detecting an electronic communication of the first set of electronic communications, the electronic communications comprising an electronic identifier of a load, wherein the load identifiers comprises the electronic identifier of the load;
consequent to detecting the electronic identifier, retrieving, via at least one data storage server of the one or more data storage servers and based at least in part on the electronic identifier, a characteristic of the load from an electronic record stored in the unified data layer;
identifying, by the transformative integration engine, i) a first task specification for a first task associated with the load, ii) a target time for performing the first task, and iii) a type of task-performing resource configured to accept loads having the characteristic;
accessing, by the transformative integration engine, a respective metric for each resource-allocation system in a plurality of resource-allocation systems that is indicative of a respective reliability of performance of tasks previously assigned to the resource-allocation system;
bias, based at least in part on the metrics accessed, an assignment of the first task with respect to a subset of the plurality of resource-allocation systems, and, consequent to the biasing, assigning the first task to a particular resource-allocation system from the subset;
generating, by the transformative integration engine, a first signal corresponding to the first task that identifies the target time and is indicative of the assignment of the first task;
transmitting, by the transformative integration engine, the first signal to the particular resource-allocation system;
detecting, by the transaction management engine or the transformative integration engine, one or more subsequent electronic communications comprising location-based data that is communicated from at least one of the one or more detecting components and based at least in part on one or more sensors detecting indicators of one or more locations of the task-performing resource;
predicting, by the transformative integration engine, a timeliness of performance of the first task based at least partially on the location-based data;
accessing, by the transformative integration engine, a target efficiency metric reflecting a target efficiency of task performance;
accessing, by the transformative integration engine, a flexible task schedule to identify a second task identified;
determining, by the transformative integration engine, a performance time for the second task to be performed based at least partially on the predicted timeliness of performance of the first task and the target efficiency metric;
transmitting, by the transformative integration engine, a second signal with an instruction to perform the second task at the performance time determined;
tracking, by the transformative integration engine, subsequent transmissions so that electronic communications with data corresponding to the first task and/or the second task are detected; and
generating, by the transformative integration engine, one or more alerts based at least in part on receiving tracked data.

9. The method for controlling resource allocation and task processing as recited in claim 8, wherein the one or more interfaces receive a second set of electronic communications from the one or more detecting components that are communicatively coupled to the one or more sensors, the location-based data comprising geolocation data.

10. The method for controlling resource allocation and task processing as recited in claim 9, further comprising identifying, by the transformative integration engine, the target efficiency metric based at least in part on previously stored data in the unified data layer and applying a learning technique that identifies metrics associated with positive results.

11. The method for controlling resource allocation and task processing as recited in claim 10, further comprising receiving the electronic communication of the first set of electronic communications from at least one detecting component of the one or more detecting components, wherein the at least one detecting component detects a scan of an electronic device or an electronic tag corresponding to the load.

12. The method for controlling resource allocation and task processing as recited in claim 11, the tracking subsequent transmissions comprising:
 identifying a first time corresponding to performance of a defined portion of the first task;
 comparing the first time to a target time; and
 adjusting the respective metric for the particular resource-allocation system based at least partially on the comparison of the first time to the target time, wherein the respective metric comprises a metric for task performance.

13. The method for controlling resource allocation and task processing as recited in claim 12, wherein the biasing the assignment of the first task comprises selecting the subset of the plurality of resource-allocation systems, the selection being at least partially based on the metrics accessed, and selectively transmitting one or more allocation requests to each resource-allocation system in the subset.

14. The method for controlling resource allocation and task processing as recited in claim 13, wherein the selectively transmitting the allocation requests to each resource-allocation system in the subset comprises sequentially transmitting each allocation requests of a plurality of allocation requests to one or more of the resource-allocation systems of the plurality of resource-allocation systems according to a ranked order.

15. One or more non-transitory, machine-readable media having machine-readable instructions thereon which, when executed by a system for controlling resource allocation and task processing, implements a method comprising:
 aggregating, by a transformative integration engine communicatively coupled with a transaction management engine, data from one or more detecting components, the transformative integration engine comprising one or more aggregation servers communicatively coupled to the one or more detecting components;
 storing, by one or more data storage servers of the transformative integration engine, the data aggregated in a unified data layer;
 receiving, via one or more interfaces, a first set of electronic communications from one or more detection devices that detect load identifiers;
 tracking, by the transaction management engine, transmissions of electronic communications communicated via the one or more interfaces, the tracking transmissions comprising detecting an electronic communication of the first set of electronic communications, the electronic communications comprising an electronic identifier of a load, wherein the load identifiers comprises the electronic identifier of the load;
 consequent to detecting the electronic identifier, retrieving, via at least one data storage server of the one or more data storage servers and based at least in part on the electronic identifier, a characteristic of the load from an electronic record stored in the unified data layer;
 identifying, by the transformative integration engine, i) a first task specification for a first task associated with the load, ii) a target time for performing the first task, and iii) a type of task-performing resource configured to accept loads having the characteristic;
 accessing, by the transformative integration engine, a respective metric for each resource-allocation system in a plurality of resource-allocation systems that is indicative of a respective reliability of performance of tasks previously assigned to the resource-allocation system;
 bias, based at least in part on the metrics accessed, an assignment of the first task with respect to a subset of the plurality of resource-allocation systems, and, consequent to the biasing, assigning the first task to a particular resource-allocation system from the subset;
 generating, by the transformative integration engine, a first signal corresponding to the first task that identifies the target time and is indicative of the assignment of the first task;
 transmitting, by the transformative integration engine, the first signal to the particular resource-allocation system;
 detecting, by the transaction management engine or the transformative integration engine, one or more subsequent electronic communications comprising location-based data that is communicated from at least one of the one or more detecting components and based at least in part on one or more sensors detecting indicators of one or more locations of the task-performing resource;
 predicting, by the transformative integration engine, a timeliness of performance of the first task based at least partially on the location-based data;
 accessing, by the transformative integration engine, a target efficiency metric reflecting a target efficiency of task performance;
 accessing, by the transformative integration engine, a flexible task schedule to identify a second task identified;
 determining, by the transformative integration engine, a performance time for the second task to be performed based at least partially on the predicted timeliness of performance of the first task and the target efficiency metric;
 transmitting, by the transformative integration engine, a second signal with an instruction to perform the second task at the performance time determined;
 tracking, by the transformative integration engine, subsequent transmissions so that electronic communications with data corresponding to the first task and/or the second task are detected; and
 generating, by the transformative integration engine, one or more alerts based at least in part on receiving tracked data.

16. The one or more non-transitory, machine-readable media as recited in claim 15, wherein the one or more interfaces receive a second set of electronic communications from the one or more detecting components that are communicatively coupled to the one or more sensors, the location-based data comprising geolocation data.

17. The one or more non-transitory, machine-readable media as recited in claim 16, further comprising identifying, by the transformative integration engine, the target efficiency metric based at least in part on previously stored data in the unified data layer and applying a learning technique that identifies metrics associated with positive results.

18. The one or more non-transitory, machine-readable media as recited in claim 17, further comprising receiving the electronic communication of the first set of electronic communications from at least one detecting component of the one or more detecting components, wherein the at least one detecting component detects a scan of an electronic device or an electronic tag corresponding to the load.

19. The one or more non-transitory, machine-readable media as recited in claim 18, the tracking subsequent transmissions comprising:
   identifying a first time corresponding to performance of a defined portion of the first task;
   comparing the first time to a target time; and
   adjusting the respective metric for the particular resource-allocation system based at least partially on the comparison of the first time to the target time, wherein the respective metric comprises a metric for task performance.

20. The one or more non-transitory, machine-readable media as recited in claim 19, wherein the biasing the assignment of the first task comprises selecting the subset of the plurality of resource-allocation systems, the selection being at least partially based on the metrics accessed, and selectively transmitting one or more allocation requests to each resource-allocation system in the subset.

* * * * *